(12) United States Patent
Raleigh et al.

(10) Patent No.: US 10,072,060 B2
(45) Date of Patent: Sep. 11, 2018

(54) ISLET AMYLOID POLYPEPTIDES WITH IMPROVED SOLUBILITY

(71) Applicant: THE RESEARCH FOUNDATION FOR THE STATE UNIVERSITY OF NEW YORK, Albany, NY (US)

(72) Inventors: Daniel Raleigh, Stony Brook, NY (US); Hui Wang, East Setauket, NY (US); Ping Cao, New York, NY (US); Andisheh Abedini, New York, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/308,138

(22) PCT Filed: May 1, 2015

(86) PCT No.: PCT/US2015/028683
§ 371 (c)(1),
(2) Date: Nov. 1, 2016

(87) PCT Pub. No.: WO2015/168488
PCT Pub. Date: Nov. 5, 2015

(65) Prior Publication Data
US 2017/0051032 A1    Feb. 23, 2017

Related U.S. Application Data

(60) Provisional application No. 61/987,723, filed on May 2, 2014.

(51) Int. Cl.
| | | |
|---|---|---|
| *A61K 38/28* | (2006.01) | |
| *A61K 38/22* | (2006.01) | |
| *A61K 38/00* | (2006.01) | |
| *C07K 14/00* | (2006.01) | |
| *C07K 14/575* | (2006.01) | |

(52) U.S. Cl.
CPC .......... *C07K 14/575* (2013.01); *A61K 38/22* (2013.01); *A61K 38/28* (2013.01); *C07K 14/001* (2013.01); *A61K 38/00* (2013.01)

(58) Field of Classification Search
CPC .... A61K 38/28; A61K 2300/00; A61K 38/00; A61K 38/22; C07K 14/00; C07K 14/001; C07K 14/575
USPC ......... 530/300, 308, 324; 514/6.3, 7.2, 11.7, 514/21.3
See application file for complete search history.

(56) References Cited

U.S. PATENT DOCUMENTS

| | | |
|---|---|---|
| 2008/0248999 A1 | 10/2008 | Steiner |
| 2010/0221240 A1 | 9/2010 | Kapurniotu et al. |
| 2010/0239554 A1* | 9/2010 | Schellenberger .... C07K 14/001 424/94.3 |
| 2017/0037088 A1* | 2/2017 | Schellenberger .... C07K 14/001 |

FOREIGN PATENT DOCUMENTS

| | | |
|---|---|---|
| WO | WO 93/10146 A1 | 5/1993 |
| WO | 99/34822 A1 | 7/1999 |
| WO | 2013/151729 A1 | 10/2013 |

OTHER PUBLICATIONS

International Search Report dated Jan. 11, 2016 issued in PCT/US2015/028683.
Cao, P et al., "Islet amyloid polypeptide toxicity and membrane interactions", PNAS (Nov. 26, 2013), vol. 110, No. 48, pp. 19279-19284.
Brender, JR et al., "A Single Mutation in the Non-Amyloidogenic Region of IAPP (Amylin) Greatly Reduces Toxicity", NIH Public Access Author Manuscript, PMC, Dec. 2, 2009; 19 pages; published in final edited form as: Biochemistry, Dec. 2, 2008, vol. 47, No. 48, pp. 12680-12688.
Fox, A. et al., "Selection for NonamyloidogenIc Mutants of Islet Amyloid Polypeptide (IAPP) Identifies an Extended Region for Amyloldogenicity", Biochemistry, Published online Aug. 10, 2010, vol. 49, pp. 7783-7789.
Meng, F et al., "The Combination of Kinetically Selected Inhibitors in Trans Leads to the Highly Effective Inhibition of Amyloid Formation", NIH Public Access Author Manuscript, J Am Chem Soc., available in PMC Oct. 24, 2011, 8 pages; Published in final edited form as: J Am 1-16 Chem Soc. Oct. 20, 2010, vol. 132, No. 41, pp. 14340-14342.
Chiu, C-C et al., "Effect of Proline Mutations on the Monomer Conformations of Amylin", Biophysical Journal (Sep. 2013), vol. 105, pp. 1227-1235.
Westermark, P et al., "Islet amyloid polypeptide: Pinpointing amino acid residues linked to amyloid fibril formation", Proc. Natl. Acad. Sci. USA (Jul. 1990), vol. 87, pp. 5036-5040.
Wang, H et al., "Rationally Designed, Nontoxic, Nonamyloidogenic Analogues of Human Islet Amyloid Polypeptide with Improved Solubility", Biochemistry (Aug. 20, 2014), vol. 53, pp. 5876-5884.
Extended Supplementary European Search Report dated Sep. 8, 2017 received in European Application No. 15 78 6103.0.

* cited by examiner

*Primary Examiner* — Julie Ha
(74) *Attorney, Agent, or Firm* — Scully, Scott, Murphy & Presser, P.C.

(57) ABSTRACT

Isolated non-naturally occurring, mutant-human islet amyloid polypeptides (hIAPP) are disclosed. These polypeptides can be formulated or co-formulated at physiological pH, which enable the polypeptides of the instant disclosure to be delivered to a subject having an amyloid-based disease in a single injection with an insulin agent. Methods and compositions for treating amyloid-based disease in a subject in need thereof, by administering an effective amount of an isolated, mutant-hIAPP polypeptide, including formulations or co-formulations thereof are also disclosed.

6 Claims, 9 Drawing Sheets
(6 of 9 Drawing Sheet(s) Filed in Color)

Specification includes a Sequence Listing.

SEQ ID NO: 1 hIAPP: H₃N⁺—KCNTATCATQ RLANFLVHSS NNFGAILSS TNVGSNTY—C(=O)—NH₂

SEQ ID NO: 2 rIAPP: H₃N⁺—KCNTATCATQ RLANFLVRSS NNLGPVLPP TNVGSNTY—C(=O)—NH₂

SEQ ID NO: 3 PM: H₃N⁺—KCNTATCATQ RLANFLVHSS NNFGPILPP TNVGSNTY—C(=O)—NH₂

SEQ ID NO: 7 TM-a: H₃N⁺—KCNTATCATQ RLANFLVRSS NNFPAPLSS TNVGSNTY—C(=O)—NH₂

SEQ ID NO: 8 QM: H₃N⁺—KCNTATCATQ RLANFLVRSS NNFGPILPP TNVGSNTY—C(=O)—NH₂

SEQ ID NO: 9 TM-b: H₃N⁺—KCNTATCATQ RLANFLVHSR NNFPAPLSS TNVGSNTY—C(=O)—NH₂

SEQ ID NO: 11 DM: H₃N⁺—KCNTATCATQ RLANFLVRSS NNFGAPLSS TNVGSNTY—C(=O)—NH₂

FIGURE 1

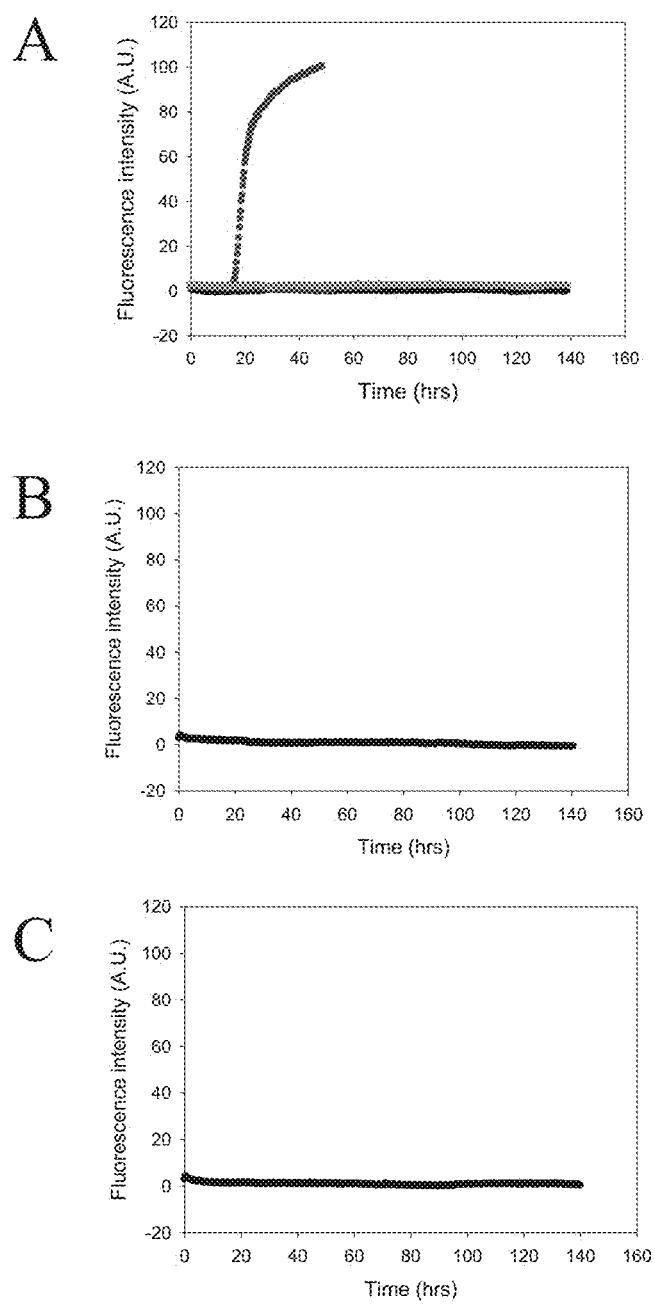
FIGURES 2A-C

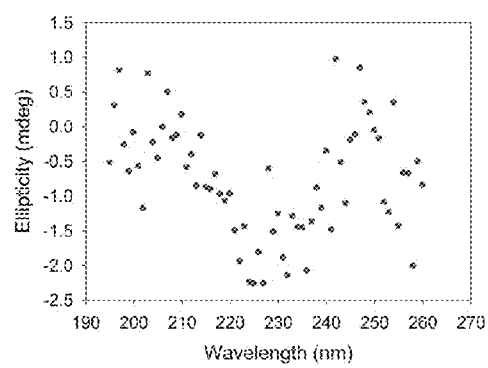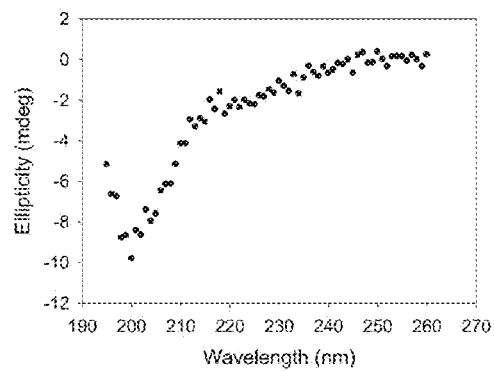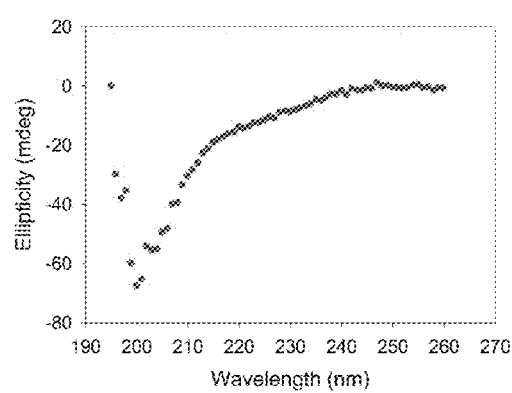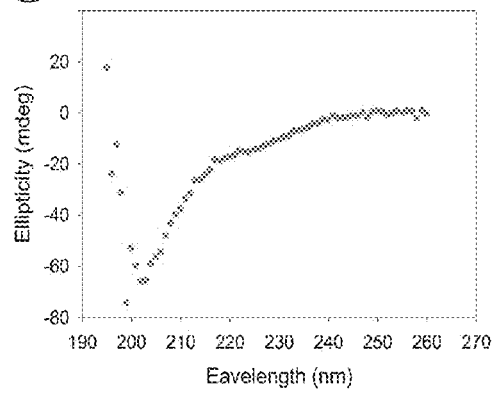
FIGURES 2D-G

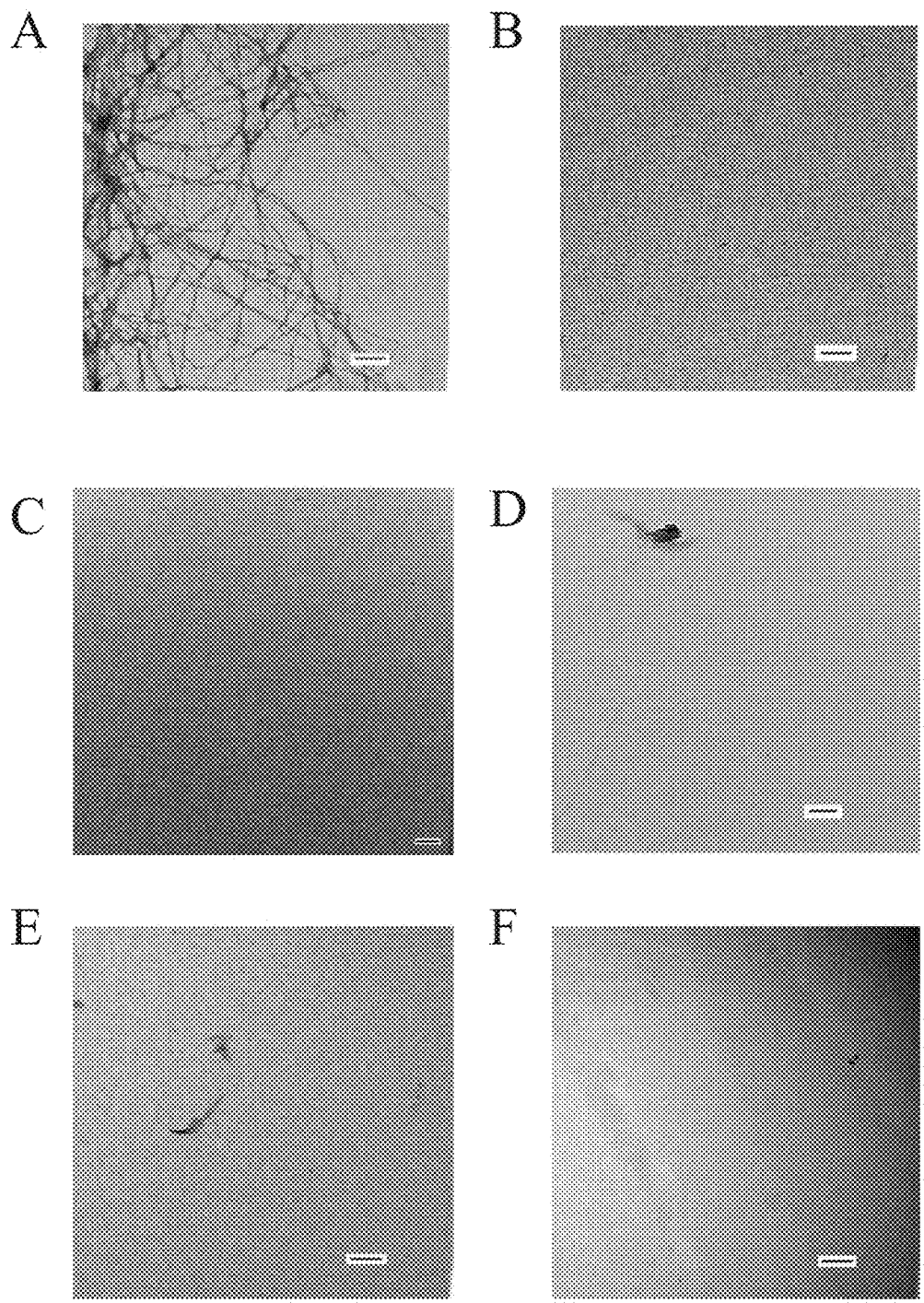
FIGURES 3A-F

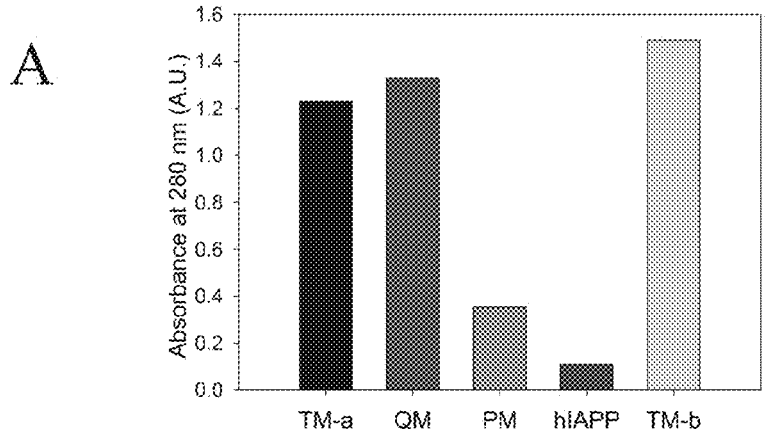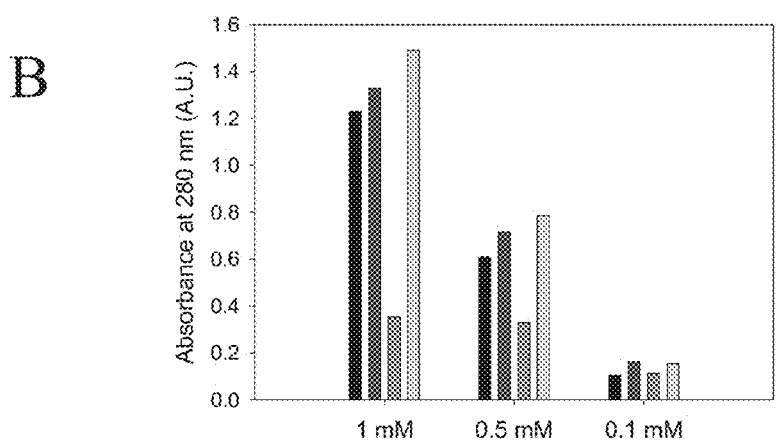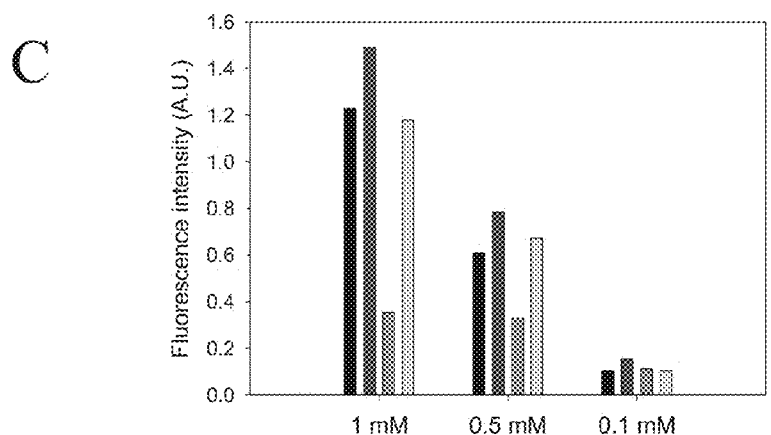
FIGURES 4A-C

Figure 5C:
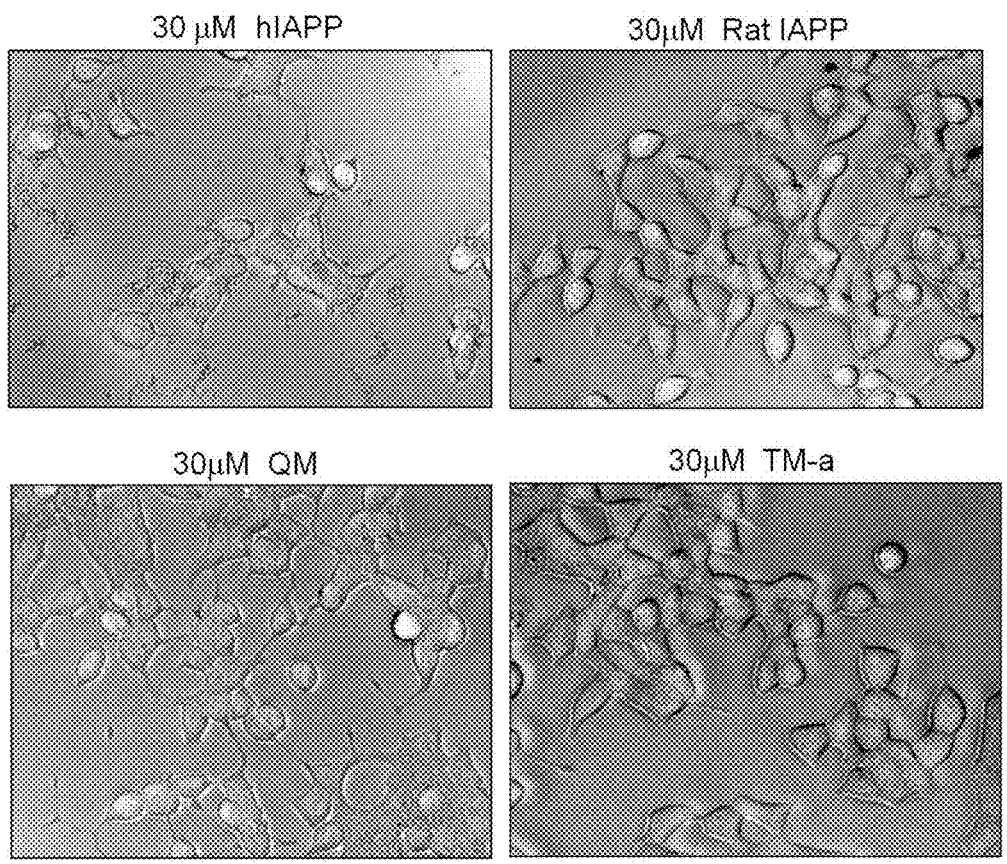

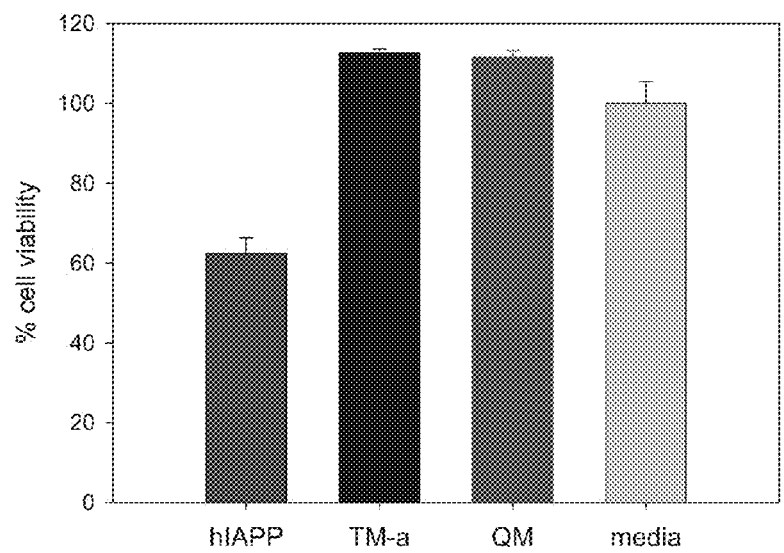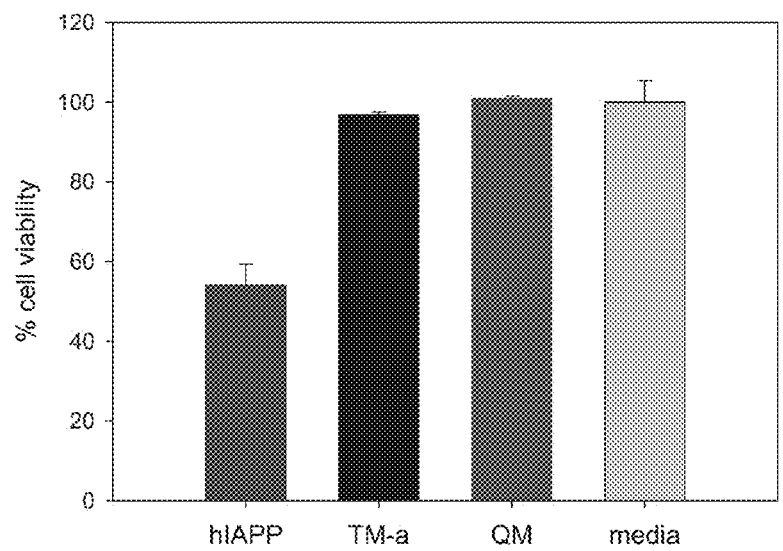
FIGURES 5A-B

Figure 6C:
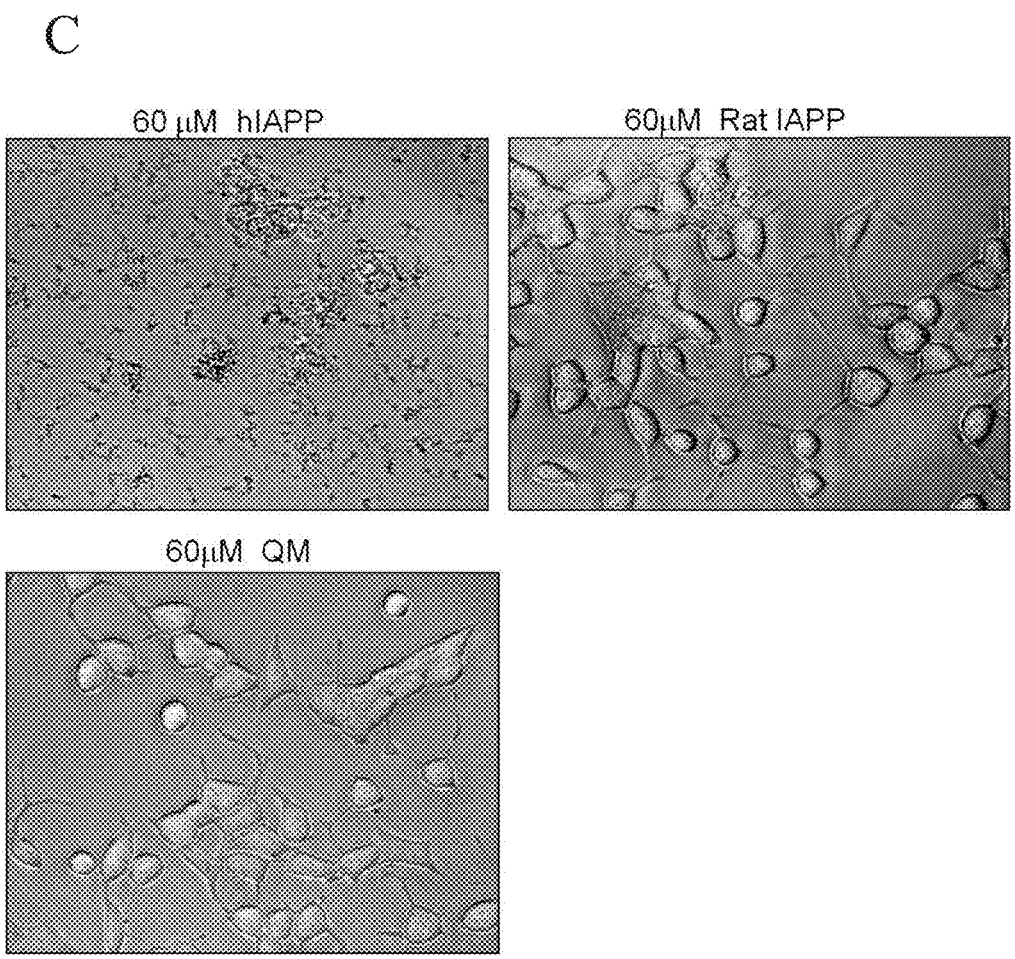

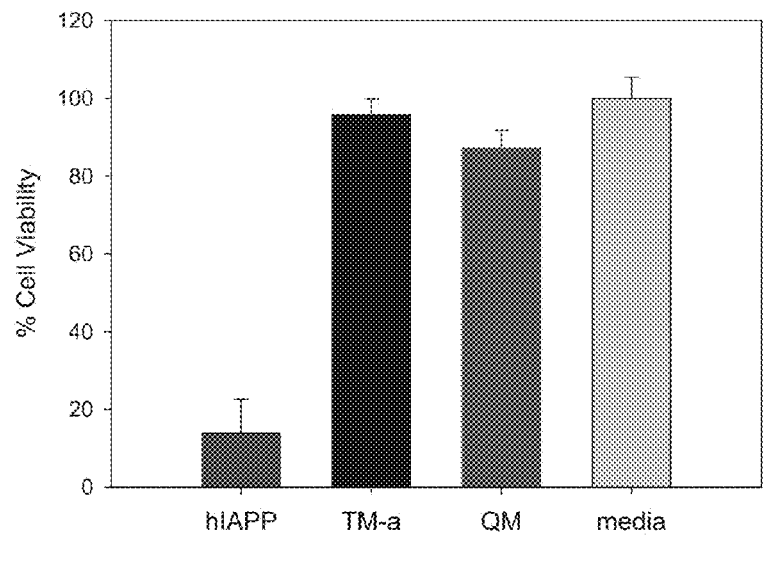
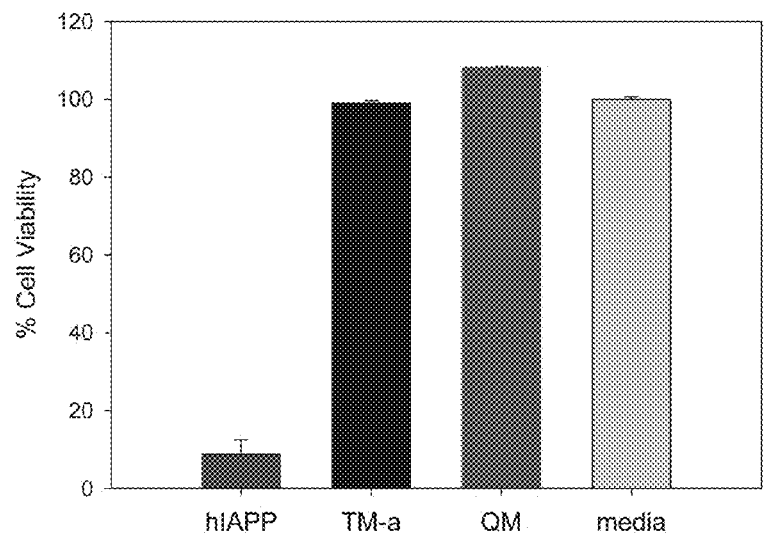
FIGURES 6A-B

2

SEQUENCE LISTING

<160> NUMBER OF SEQ ID NOS: 11

<210> SEQ ID NO 1
<211> LENGTH: 37
<212> TYPE: PRT
<213> ORGANISM: Homo sapiens
<220> FEATURE:
<221> NAME/KEY: MOD_RES
<222> LOCATION: (37)..(37)
<223> OTHER INFORMATION: AMIDATION,

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val

-continued

```
            20                  25                  30

Gly Ser Asn Thr Tyr
        35

<210> SEQ ID NO 2
<211> LENGTH: 37
<212> TYPE: PRT
<213> ORGANISM: Rattus rattus
<220> FEATURE:
<221> NAME/KEY: MOD_RES
<222> LOCATION: (37)..(37)
<223> OTHER INFORMATION: AMIDATION,

<400> SEQUENCE: 2

Lys Cys Asn Thr Ala Thr Cys Ala Thr Gln Arg Leu Ala Asn Phe Leu
1               5                   10                  15

Val Arg Ser Ser Asn Asn Phe Gly Pro Val Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: mutant human islet amyloid precursor protein
      analog, pramalintide
<220> FEATURE:
<221> NAME/KEY: MOD_RES
<222> LOCATION: (37)..(37)
<223> OTHER INFORMATION: AMIDATION,

<400> SEQUENCE: 3

Lys Cys Asn Thr Ala Thr Cys Ala Thr Asn Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 4
<211> LENGTH: 37
<212> TYPE: PRT
<213> ORGANISM: Artificial Sequence
<220> FEATURE:
<223> OTHER INFORMATION: mutant human islet amyloid precursor protein,
      Tm-a, having H18R, G24P and I26P amino acid substitutions

<400> SEQUENCE: 4

Lys Cys Asn Thr Ala Thr Cys Ala Thr Gln Arg Leu Ala Asn Phe Leu
1               5                   10                  15

Val Arg Ser Ser Asn Asn Phe Pro Ala Pro Leu Ser Ser Thr Asn Val
            20                  25                  30

Gly Ser Asn Thr Tyr
        35

<210> SEQ ID NO 5
<211> LENGTH: 37
<212> TYPE: PRT
<213> ORGANISM: Artificial Sequence
<220> FEATURE:
<223> OTHER INFORMATION: mutant human islet amyloid precursor protein,
      QM having H18R, A25P, S28P and S29P amino acid substitutions
```

```
<400> SEQUENCE: 5

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
        35

<210> SEQ ID NO 6
<211> LENGTH: 37
<212> TYPE: PRT
<213> ORGANISM: Artificial Sequence
<220> FEATURE:
<223> OTHER INFORMATION: mutant human islet amyloid precursor protein,
      Tm-b having S20R, G24P and I26P amino acid substitutions

<400> SEQUENCE: 6

Lys Cys Asn Thr Ala Thr Cys Ala Thr Gln Arg Leu Ala Asn Phe Leu
1               5                   10                  15

Val His Ser Arg Asn Asn Phe Pro Ala Pro Leu Ser Ser Thr Asn Val
            20                  25                  30

Gly Ser Asn Thr Tyr
        35

<210> SEQ ID NO 7
<211> LENGTH: 37
<212> TYPE: PRT
<213> ORGANISM: Artificial Sequence
<220> FEATURE:
<223> OTHER INFORMATION: mutant human islet amyloid precursor protein
      analog, Tm-a, having H18R, G24P and I26P amino acid substitutions
      and an amidated c-terminal
<220> FEATURE:
<221> NAME/KEY: MOD_RES
<222> LOCATION: (37)..(37)
<223> OTHER INFORMATION: AMIDATION,

<400> SEQUENCE: 7

Lys Cys Asn Thr Ala Thr Cys Ala Thr Gln Arg Leu Ala Asn Phe Leu
1               5                   10                  15

Val Arg Ser Ser Asn Asn Phe Pro Ala Pro Leu Ser Ser Thr Asn Val
            20                  25                  30

Gly Ser Asn Thr Tyr
        35

<210> SEQ ID NO 8
<211> LENGTH: 37
<212> TYPE: PRT
<213> ORGANISM: Artificial Sequence
<220> FEATURE:
<223> OTHER INFORMATION: mutant human islet amyloid precursor protein
      analog, QM having H18R, A25P, S28P and S29P amino acid
      substitutions and an amidated c-terminal
<220> FEATURE:
<221> NAME/KEY: MOD_RES
<222> LOCATION: (37)..(37)
<223> OTHER INFORMATION: AMIDATION,

<400> SEQUENCE: 8

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
            20                  25                  30

Gly Ser Asn Thr Tyr
```

```
<210> SEQ ID NO 9
<211> LENGTH: 37
<212> TYPE: PRT
<213> ORGANISM: Artificial Sequence
<220> FEATURE:
<223> OTHER INFORMATION: mutant human islet amyloid precursor protein
      analog, Tm-b having S20R, G24P and I26P amino acid substitutions
      and an amidated c-terminal
<220> FEATURE:
<221> NAME/KEY: MOD_RES
<222> LOCATION: (37)..(37)
<223> OTHER INFORMATION: AMIDATION,

<400> SEQUENCE: 9

Lys Cys Asn Thr Ala Thr Cys Ala Thr Gln Arg Leu Ala Asn Phe Leu
1               5                   10                  15

Val His Ser Arg Asn Asn Phe Pro Ala Pro Leu Ser Ser Thr Asn Val
            20                  25                  30

Gly Ser Asn Thr Tyr
        35

<210> SEQ ID NO 10
<211> LENGTH: 37
<212> TYPE: PRT
<213> ORGANISM: Artificial Sequence
<220> FEATURE:
<223> OTHER INFORMATION: mutant human islet amyloid precursor protein,
      DM having H18R and I26P amino acid substitutions

<400> SEQUENCE: 10

Lys Cys Asn Thr Ala Thr Cys Ala Thr Gln Arg Leu Ala Asn Phe Leu
1               5                   10                  15

Val Arg Ser Ser Asn Asn Phe Gly Ala Pro Leu Ser Ser Thr Asn Val
            20                  25                  30

Gly Ser Asn Thr Tyr
        35

<210> SEQ ID NO 11
<211> LENGTH: 37
<212> TYPE: PRT
<213> ORGANISM: Artificial Sequence
<220> FEATURE:
<223> OTHER INFORMATION: mutant human islet amyloid precursor
      polypeptide analog, DM having H18R and I26P amino acid
      substitutions and an amidated c-terminal
<220> FEATURE:
<221> NAME/KEY: MOD_RES
<222> LOCATION: (37)..(37)
<223> OTHER INFORMATION: AMIDATION,

<400> SEQUENCE: 11

Lys Cys Asn Thr Ala Thr Cys Ala Thr Gln Arg Leu Ala Asn Phe Leu
1               5                   10                  15

Val Arg Ser Ser Asn Asn Phe Gly Ala Pro Leu Ser Ser Thr Asn Val
            20                  25                  30

Gly Ser Asn Thr Tyr
        35
```

ISLET AMYLOID POLYPEPTIDES WITH IMPROVED SOLUBILITY

CROSS REFERENCE TO RELATED APPLICATIONS

This application claims priority from U.S. Provisional Application No. 61/987,723 filed May 2, 2014, the entire contents of which are incorporated herein by reference.

STATEMENT REGARDING FEDERALLY SPONSORED RESEARCH

This invention was made with government support under grant number GM078114 awarded by the National Institute of Health. The government has certain rights in the invention.

INCORPORATION BY REFERENCE OF SEQUENCE LISTING

The Sequence Listing in the ASCII text file, named as R8333_R8518_US_FOA_SubstituteSequenceListing.txt of 11 KB, created on Apr. 27, 2018, and submitted to the United States Patent and Trademark Office via EFS-Web, is incorporated herein by reference.

FIELD OF THE DISCLOSURE

This disclosure relates generally, to the design, generation and isolation of, rationally designed human islet amyloid polypeptides (hIAPP also known as human amylin and amylin). Specifically, the present disclosure provides mutant-hIAPP polypeptides that are soluble at physiological pH. Further, the mutant-hIAPP polypeptides of the present disclosure do not aggregate or form amyloid fibrils, and are non-toxic compared to endogenous hIAPP polypeptides. The instant disclosure also provides methods for using the mutant-hIAPP polypeptides of the present disclosure to treat various amyloid-based pathologies including, but not limited to, type 1, type 2 and mature diabetes of the young. In certain embodiments of the present disclosure, the mutant-hIAPP polypeptides are co-formulated with insulin or other therapeutic agents at neutral pH for the treatment of amyloid based diseases.

BACKGROUND OF THE DISCLOSURE

Insulin therapy is the most widely used clinical treatment for diabetes. Despite improvements in insulin therapy over the past few decades, the goal of reinstating complete physiological glucose homeostasis in diabetes patients have not been achieved. In particular, postprandial hyperglycemia remains an obstacle even with aggressive insulin therapy; in part because diabetes is a multihormonal disease, which involves the disturbed secretion of several hormones that physiologically, work in synergy to achieve normal glycemic control. See Kruger et al., *Drugs* (2004) 64 pp. 1419-1432.

Human islet amyloid polypeptide (hIAPP or amylin) is a neuroendocrine hormone produced in the pancreatic β-cells, which is stored in the insulin secretory granule and co-secreted with insulin. See Cooper, G. J. et al., *Proc. Natl. Acad. Sci.* (1987) Vol. 84 pp. 8628-8632; and Clark, A. et al., *Lancet* (1987) Vol. 2, pp. 231-234. In non-diabetic subjects, hIAPP complements the effects of insulin in postprandial glycemic control by suppressing glucagon secretion, and by helping regulate the rate of gastric emptying, and by inducing satiety to suppress food intake. See Scherbaum, W. A. *Exp. Clin. Endocr. Diab.* (1998) Vol. 106, pp. 97-102; and Rushing, P. A. et al., *Endocrinology* (2001) Vol. 142, pp. 5035-5038. hIAPP forms amyloid in the pancreatic islets of Langerhans in diabetes by an unknown mechanism. Pancreatic hIAPP amyloid deposits, are associated with reduced β-cell mass and contribute to type 2 diabetes and islet transplant failure. See Westermark, P., and Wilander, E. *Diabetologia* (1978) Vol. 15, pp. 417-421; Westermark, P. et al. *Am. J. Pathol.* (1987) Vol. 127, pp. 414-417; Westermark, P., Andersson, A., and Westermark, G. T. *Physiol Rev* (2011) Vol. 91, pp. 795-826; Cao P., Abedini A., Raleigh D. P. *Curr. Opin. Struct. Biol.* (2013) Vol. 23, pp. 82-88; and Potter, K. J., et al. *Proc. Natl Acad. Sci.* (2010) Vol. 107, pp. 4305-4310.

While hIAPP is deficient in both type 1 and type 2 diabetes patients (see Koda, J. E. et al., *Lancet* (1992) Vol. 339, pp. 1179-1180), clinical use of hIAPP is impractical because of its aggressive tendency to aggregate, which causes difficulties in formulation and storage and importantly, aggregates formed during hIAPP amyloid formation are toxic. A more soluble analog of hIAPP, pramlintide, i.e., Symlin™ (PM), has been developed and approved by the FDA, in which amino acid residues 25, 28, and 29 of endogenous hIAPP were substituted with proline. The substitution of the three prolines renders the hIAPP polypeptide non-amyloidgenic. However, pramlintide is not soluble at physiological pH. See Kruger et al., *Drugs* (2004) Vol. 64, pp. 1419-1432. Therefore, co-formulation of insulin, or an analog thereof, with pramlintide is not possible because hIAPP and pramlindtide are soluble at acidic pH (i.e., pH of about 4.0), whereas certain insulin agents, i.e., Humalog®, Apidra®, NovoLog®, Humulin®, Novolin®, Levemir® are formulated at near neutral pH (i.e., pH 7.0-7.8). This phenomenon requires separate injections of the pramlintide and insulin, leading to increased cost and reduced patient compliance.

SUMMARY OF THE DISCLOSURE

Mature hIAPP is composed of 37 amino acid residues with an amidated C-terminus and a disulfide bond between Cys-2 and Cys-7 (see FIG. 1). The polypeptide is more soluble at acidic pH than at neutral pH and is highly amyloidgenic under physiological conditions.

In certain aspects of the present disclosure, rationally designed synthetic analogs of hIAPP polypeptides (mutant-hIAPP) are prepared, which exhibit increased solubility at neutral pH, are non-toxic to β-cells and do not form amyloid fibrils (i.e., fail to aggregate). In certain embodiments, the mutant-hIAPP polypeptides of the instant disclosure contain at least one amino acid substitution at position: 18, 20, 24, 25, 26, 28 or 29. In another embodiment, the mutant-hIAPP polypeptides of the present disclosure contain the following amino acid substitution: H18R, S20R, G24P, A25P, I26P, S28P, S29P or any combination thereof.

In certain specific embodiments of the present disclosure, the mutant-hIAPP polypeptides include at least the following amino acid substitutions: H18R, G24P, and I26P. In yet another embodiment of the present disclosure, the mutant-hIAPP polypeptides include at least the following amino acid substitutions: S20R, G24P, and I26P. In yet another embodiment of the present disclosure, the mutant-hIAPP polypeptides include at least the following amino acid substitutions: H18R, A25P, S28P, S29P. In specific embodiments the mutant-hIAPP polypeptide includes amino acid substitutions H18R, G24P, and I26P as set forth in SEQ ID NO: 4. In specific embodiments, the mutant-hIAPP polypeptide include amino acid substitutions S20R, G24P, and I26P as set forth in SEQ ID NO: 5. In yet another specific embodiment of the present disclosure, the mutant-hIAPP polypeptide include amino acid substitutions H18R, A25P, S28P and S29P as set forth in SEQ ID NO: 6. In certain embodiments the mutant-hIAPP polypeptides of the present disclosure include N-Methyl Glycine at position 24 and a positively charged amino acid substitution at residue 18 and/or 20 (e.g., H18R, S20R). In yet another embodiment the mutant-hIAPP polypeptides include N-Methyl Isoleucine at position 26 and a positively charged amino acid substitution at residue 18 and/or 20 (e.g., H18R, S20R).

In other embodiments, the mutant-hIAPP polypeptides of the present disclosure include a positively charged amino acid substitution at residue 18 and/or 20 (e.g., H18R, S20R) and a single proline residue substitution at a position 24, 25, 26, 28 or 29 (e.g., G24P, A25P, I26P, S28P, S29P). In certain specific embodiments the mutant-hIAPP polypeptides of the present disclosure include a positively charged amino acid substitution at residue 18 and/or 20 (e.g., H18R, S20R) and a single proline residue substitution at a position 24, 25, 26, 28 or 29 (e.g., G24P, A25P, I26P, S28P, S29P).

In another preferred aspect, the mutant-hIAPP polypeptides of the present disclosure are formulated in a neutral form (i.e., physiological pH or pH 7.0-7.6).

In certain aspects of the present disclosure, the mutant-hIAPP polypeptide compositions disclosed herein are co-formulated with at least one other therapeutic agent (e.g., Humalog®, Apidra®, NovoLog®, Humulin®, Novolin®, Levemir® or combinations thereof) at neutral pH. In certain embodiments, the mutant-hIAPP polypeptides of the instant disclosure are co-formulated at a neutral pH with insulin and provided to a subject having an amyloid-based disease, such as diabetes (e.g., type 1, type 2, mature diabetes of the young and gestational diabetes), hyperglycemia or amyloidoses.

BRIEF DESCRIPTION OF DRAWINGS AND TABLES

The file of this patent contains at least one drawing executed in color. Copies of this patent with color drawing(s) will be provided by the Patent and Trademark Office upon request and payment of the necessary fee.

FIG. 1. Sequence of human-IAPP, rat-IAPP, Pramlintide (PM), TM-a, TM-b, QM and DM. Each polypeptide has a disulfide bond connecting Cys 2 and Cys 7 and an amidated C-terminus. TM-a includes the following residue changes: H18R, G24P, and I26P, as set forth in SEQ ID NO: 7), while polypeptide QM includes residue changes H18R, A25P, S28P, S29P, as set forth in SEQ ID NO: 8), TM-b includes residue changes S20R, G24P, I26P, as set forth in SEQ ID NO: 9), and DM includes the H18R and I26P, as set forth in SEQ ID NO: 11), when compared to the wild-type human-IAPP set forth in SEQ ID NO: 1). The rat-IAPP amino acid sequence set forth in SEQ ID NO: 2 is also depicted. Mutated amino acid residues, which differ from that of wild-type human LAPP are shown in red.

FIG. 2. The kinetics of amyloid formation by hIAPP, TM-a,b, QM and PM monitored by thioflavin-T fluorescence assays. (A) The kinetics of amyloid formation by the following mutant hIAPP peptides: hIAPP (blue); TM-a (black); QM (red); PM (green). The black, red and green curves overlap revealing that the mutant-hIAPP polypeptides of the present disclosure do not form amyloid. (B) TM-b does not form amyloid during the time course of the experiments. The concentration of TM-b was 160 µM. (C) DM does not form amyloid during the time course of the experiments. The kinetic experiments were conducted in 20 mM Tris-HCl (pH 7.4) without stirring at 25° C. The concentration of hIAPP was 16 µM. The concentration of all other peptides was 160 µM each. CD spectra of aliquots of (D) hIAPP, (E) TM-a, (F) QM and (G) PM taken at the end of each kinetic experiment were shown in FIG. 2. The β-sheet secondary structure shown in panel B reflect the fact that hIAPP formed amyloid.

FIG. 3. TEM images showing the protein morphology of IAPP samples. Images were recorded of aliquots of (A) hIAPP, (B) TM-a, (C) QM, (D) PM, (E) TM-b and (F) DM samples collected at the end of each kinetic experiment shown in FIG. 2. Scale bars represent 100 nm.

FIG. 4. Comparison of the apparent solubility of TM-a, TM-b, QM, PM, DM and hIAPP. (A) Amount of peptide remaining in the supernatant of samples of TM-a, QM, PM, TM-b and hIAPP prepared at an initial concentration of 1 mM. (B) Comparison of the apparent solubility of TM-a (black), QM (red), PM (green) and TM-b (yellow). (C) Comparison of the apparent solubility of samples of TM-a, TM-b, PM and DM prepared at different initial concentrations. Black, TM-a; red, TM-b, green; PM, yellow, DM. The apparent solubility of the different peptides in (B)-(C) in PBS buffer at pH 7.4 is represented by absorbance at 280 nm and was measured after 7 days. The absorbance was measured after centrifugation at 24° C. for 20 min The relative centrifugal force used was $1.75 \times 10^4$ g.

FIG. 5. Comparison of the cell toxicity induced by hIAPP, TM-a and QM at 30 µM peptide concentration. (A) Cell viability after 24 hr incubation of the peptides with β-cells as judged by AlmarBlue Assays (B) Cell viability after 48 hr incubation of the peptides with β-cells as judged by Almar-Blue assays. The error bars represent the standard deviation determined from 4 repeated measurements. (C) Changes in cell morphology were examined by light microscopy to further establish that mutant-hIAPP polypeptides did not lead to apoptosis, while treatment of cells with hIAPP did. Rat IAPP is nontoxic and nonamyloidogenic and is used as a negative control in these experiments. Transformed rat INS-1 β-cells were photographed after 5 hours of incubation with 30 µM peptide concentration, prior to assessment of toxicity by AlamarBlue cell viability assays.

FIG. 6. hIAPP is toxic to INS-1 β-cells, but TM-a and QM are not. Cell toxicity of hIAPP, TM-a and QM was measured with a peptide concentration of 60 µM. (A) Cell viability after 24 hr incubation of the peptides with cells as judged by AlmarBlue Assays. (B) Cell viability after 48 hr incubation of the peptides with cells as judged by AlmarBlue assays. The error bars represent the standard deviation determined from 4 repeated measurements. (C) Changes in cell morphology were examined by light microscopy to further establish that mutant-hIAPP polypeptides did not lead to apoptosis, while treatment of cells with hIAPP resulted in cell death. Rat LAPP was used as a negative control. Transformed rat INS-1 β-cells were photographed after 5 hours of incubation with 60 µM peptide concentration, prior to assessment of toxicity by AlamarBlue cell viability assays.

DETAILED DESCRIPTION OF THE DISCLOSURE

Human islet amyloid polypeptide (hIAPP) or amylin is coproduced with insulin in the islet â-cells of the pancreas and acts as a hormone involved in the regulation of adiposity and carbohydrate metabolism. The mature, wild-type hIAPP polypeptide is 37 amino acid residues in length as set forth in SEQ ID NO: 1 and has a Cys-2 to Cys-7 disulfide bridge and an amidated C-terminus. Under normal physiological conditions, amylin is co-secreted with insulin into the circulation as a soluble monomer and excreted from the body by the kidney. hIAPP is the major protein component of amyloid plaques, which develop in pancreatic islets of type 2 diabetic patients. Moreover, the process of amyloid formation is toxic to insulin-producing β-cells, leading to islet cell stress, dysfunction and death, as well as islet transplant failure in subjects with diabetes.

Definitions

In general, the terms used herein comport with their usage by persons of skill in the field of the present disclosure. To facilitate an understanding of the embodiments of the disclosure as herein described, a number of terms, set off in quotation marks in this specification, are further explained herein. As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, not to limit the scope of the disclosure.

The term "agent" as used herein refers to any kind of compound or combination of compounds. In one embodiment of the present disclosure the agent is a small molecule. In another embodiment of the disclosure, the agent is a biological molecule, including, but not limited to, a protein or a polypeptide or a nucleic acid.

In the context of this disclosure, the term "small molecule" refers to small organic compounds, such as heterocycles, peptides, saccharides, steroids, and the like. The small molecule modulators preferably have a molecular weight of less than about 1500 Daltons, and more preferably less than 500 Daltons. The compounds can be modified to enhance efficacy, stability, pharmaceutical compatibility, and the like. Candidate modulator compounds from libraries of synthetic or natural compounds can be screened. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds can be further modified through conventional chemical and biochemical techniques.

The term "peptide", "polypeptide" or "protein" refers to a linear series of amino acid residues linked to one another by peptide bonds between the alpha-amino and carboxy groups of adjacent amino acid residues.

The term "isolated" and "purified", when used in reference to a molecule (such as a peptide, protein or polypeptide), means that the molecule has been removed from its naturally occurring environment and is substantially free of other molecules (such as other proteins). By "substantially free" of other proteins, it is meant that a protein of interest accounts for at least 60%, 70%, 80%, 90%, or 95% (by dry weight) of total proteins in a composition. When an isolated protein is recombinantly produced, it can also be substantially free of culture medium, i.e., culture medium represents less than about 20% of the volume of the preparation, less than about 10% of the volume of the preparation or less than about 5% of the volume of the preparation. For example, the mutant-hIAPP polypeptides of the present disclosure can be purified to homogeneity or other varying degrees of purity. The level of purification can be based on the intended use. In certain non-limiting examples, the isolated mutant-hIAPP polypeptides of the present disclosure can be purified from cells that express such protein, as further described below, or can be synthetically made using known protein synthesis methods.

The term "synthetic peptide" or "synthetic polypeptide" as used herein refers to a chemically derived chain of amino acid residues linked together by peptide bonds that are isolated or substantially isolated from other materials or elements. Certain non-limiting examples of synthetic peptide production methods include, solid-phase peptide synthesis, Solid-Phase Peptide Synthesis by FMOC (Fluorenylmethyloxycarbonyl) Chemistry and Solid-Phase Peptide Synthesis by t-BOC (tert-butyloxycarbonyl) Chemistry (also referred to as BOC chemistry).

The term "recombinantly-produced" as used herein generally refers to transfecting cells with a DNA vector that contains the a nucleotide sequence that coincides with the protein of interest (i.e., mutant-hIAPP polypeptide), culturing the cells so that the DNA of interest is transcribed and translated the desired protein. Cells can then be lysed to extract the expressed protein of interest for subsequent isolation and purification. Both prokaryotic and eukaryotic in vivo protein expression systems are widely used and will be known by those of ordinary skill in the art. In certain embodiments recombinantly-produced proteins may be developed using cell-free or in vitro synthesis methods. Such cell-free methods generally include whole cell extracts containing all the macromolecule components needed for transcription, translation and post-translational modification. These components include RNA polymerase, regulatory protein factors, transcription factors, ribosomes, and tRNA, which when supplemented with cofactors, nucleotides and the specific gene template containing a coding sequence that corresponds to the protein of interest (i.e., mutant-hIAPP polypeptide), these extracts synthesize the desired proteins.

The term "wild-type hIAPP", "amylin" or "Islet Amyloid Polypeptide (IAPP)", as used herein means a polypeptide including the first 37 amino acids of the human peptide hormone of Accession no. AAA35524. For example, wild-type hIAPP polypeptides of the present disclosure include the amino acid sequence KCNTATCATQRLANFLVHSSNNFGAILSSTNVGSNTY-(NH2) (SEQ ID NO: 1). Where -(NH2) indicates an amidated c-terminal amino acid. The term "amylin" or "hIAPP" also includes homologs and analogs of amylin as present in, and in isolatable form, other mammalian species.

By "homologs" it is meant that the corresponding amylin proteins of other vertebrate species are substantially homologous at the overall protein (i.e., mature protein) level to hIAPP. In certain embodiments, homologs of a hIAPP polypeptides have an amino acid sequence substantially identical to the human wild-type hIAPP polypeptide, i.e., at least 80-85%, at least 90-95% or more sequence identity. Further, homologs of hIAPP proteins retain the same physiological effects as wild-type amylin, including, for example, glucose regulation. Certain non-limiting examples of homologs of the human amylin protein include, mouse, and rat amylin. A specific example of an amylin or hIAPP homolog includes rat amylin having an amino acid sequence of KCNTATCATQRLANFLVRSSNNFGPVLPPTNVG-SNTY-(NH2) (SEQ ID NO: 2).

As used herein, the term "analog" or "amylin analog" is a molecule that has the same physiological effects as wild-type amylin, including, for example, glucose regulation, which also has one or more amino acid variations that, for example, enhance its effectiveness as a drug or increases solubility at a neutral pH, or otherwise increases its therapeutic properties, such as superior stability, solubility, efficacy, half-life, and the like. In some embodiments of the aspects described herein, an hIAPP analog is a composition that has at least 75% sequence identity to the wild-type amylin polypeptide, at least 80% sequence identity, at least 85% sequence identity, at least 90% sequence identity, or at least 95% sequence identity to wild-type amylin.

An analog can comprise a peptide having a substantially identical amino acid sequence to a peptide provided herein and in which one or more amino acid residues have been conservatively or non-conservatively substituted. Examples of a conservative substitution include the substitution of a hydrophobic residue such as isoleucine, valine, leucine or methionine or noro-leucine, or noro-valine for another. Likewise, the present disclosure contemplates the substitution of one aromatic residue such as phenylalanine, tryptophan or tyrosine for another. The substitution of a polar residue such as lysine, arginine, glutamine or asparagine for another or the substitution of a polar residue such as aspartate, glutamate, ornithine, glutamine or asparagine for another. Additionally, the present disclosure contemplates the substitution of a non-polar aliphatic residue, such as between glycine and alanine, or a polar aliphatic residue such as between serine and threonine. Examples of non-conservative substitutions include the substitution of a non-polar residue, e.g., isoleucine, valine, leucine, alanine or methionine for a polar residue e.g., glutamine, glutamate, ornithine, lysine, and/or a polar residue for a non-polar residue.

In certain specific embodiments of the compositions and methods described herein, the amylin analog is pramlintide (i.e., SYMLIN™), which has an amino acid sequence of KCNTATCATNRLANFLVHSSNNFGPILPPTNVGSNTY-(NH2) (SEQ ID NO: 3), in which the three amino acids at positions 25, 28 and 29 each are substituted to proline.

The term "mutant-hIAPP polypeptide" or "mutant-hIAPP" as used herein shall mean an amylin analog having at least 75%, at least 80%, at least 85%, at least 90%, at least 91%, at least 92% sequence identity to SEQ ID NO: 1 or SEQ ID NO: 2. For example, amylin analogs of the present disclosure include peptides having at least 75%, 76%, 77%, 78,%, 79%, 80%, 81%, 82%, 83%, 84%, 85%, 86%, 87%, 88%, 89%, 90%, 91%, and 92% sequence identity to SEQ ID NO: 1 or SEQ ID NO: 2. In certain embodiments, mutant-hIAPP polypeptides of the present disclosure include, but are not limited to, polypeptides having the amino acid sequence: KCNTATCATQRLANFLVRSSNNF-PAPLSSTNVGSNTY (SEQ ID NO: 4), KCNTATCATQR-LANFLVRSSNNFGPILPPTNVGSNTY (SEQ ID NO: 5), KCNTATCATQRLANFLVHSRNNFPAPLSSTNVGSNTY (SEQ ID NO: 6) and KCNTATCATQRLANFLVRSSNNF-GAPLSSTNVGSNTY (SEQ ID NO: 10). In certain embodiments the mutant-hIAPP polypeptides of the present disclosure have an amidated c-terminus (i.e., Y-NH$_2$). For example, mutant-hIAPP polypeptides of the present disclosure having an amidated c-terminus include KCNTAT-CATQRLANFLVRSSNNFPAPLSSTNVGSNTY-NH$_2$ (SEQ ID NO: 7), KCNTATCATQRLANFLVRSSNNFG-PILPPTNVGSNTY-NH$_2$ (SEQ ID NO: 8), KCNTAT-CATQRLANFLVHSRNNFPAPLSSTNVGSNTY-NH$_2$ (SEQ ID NO: 9), and KCNTATCATQRLANFLVRSSNN-FGAPLSSTNVGSNTY-NH$_2$ (SEQ ID NO: 11).

The term "amino acid" of "amino acid residue" as used herein shall mean natural amino acids, unnatural amino acids, and modified amino acid. Unless stated to the contrary, any reference to an amino acid, generally or specifically by name, includes reference to both the D and the L stereoisomers if their structure allow such stereoisomeric forms. For example, natural amino acids include alanine (Ala), arginine (Arg), asparagine (Asn), aspartic acid (Asp), cysteine (Cys), glutamine (Gin), glutamic acid (Glu), glycine (Gly), histidine (His), isoleucine (He), leucine (Leu), Lysine (Lys), methionine (Met), phenylalanine (Phe), proline (Pro), ornithine, serine (Ser), threonine (Thr), tryptophan (Trp), tyrosine (Tyr) and valine (Val).

The term "neutral pH" or "physiological pH" as used in the instant disclosure shall mean a solution having about the same amount of free hydrogen and hydroxide ions. The complete pH scale, which is well known in the art, ranges from a pH of about 0 (most acidic) to a pH of about 14 (most basic or alkaline). The pH of a solution may be adjusted by the addition of aqueous solutions of hydrochloric acid (e.g., 10%) to increase the acidity of a solution (i.e., lowering the pH) and/or sodium hydroxide (e.g., 10%) to increase the pH (i e , making the solution more basic). At the normal physiological temperature for humans, i.e., 37° C., neutral pH ranges from 6.8-7.6. More specifically, neutral pH formulations as used herein range from 6.8-7.4, 7.0-7.8, 7.0-7.4. In certain specific embodiments the mutant-hIAPP polypeptides of the present disclosure are formulated at a neutral pH of 7.2-7.4 or 7.4.

The term "aggregation," or "protein aggregates," used interchangeably herein, refers to a population of peptide molecules assembled into an insoluble deposit, which may have no discernible secondary structure, or may contain β-sheet structures, alpha-helices or other secondary structures. Secondary structure develops as the molecules orient themselves (evidently by intramolecular self-assembly) in strands lying side-by-side and attached by hydrogen bonds to form a so-called "β-sheet" that tends to grow along one axis into a "fibril." Fibrils are insoluble in aqueous solutions. That is, the monomers (and, perhaps, oligomers) that comprise them do not spontaneously return to their solvent as "solute" molecules. The fibrils tend to become entangled with one another to form "fibrillar tangles" and "dense core plaque," a late step in the process of fibrillization. Diffuse and dense core plaque, which may be referred to as "deposits" or "amyloid deposits," are insoluble. In certain circumstances, aggregation can occur without fibrillization of a peptide molecule and can lead to aggregates which contain other types of β-sheet structures, alpha-helical structure, or no discernable secondary structure (i.e., amorphous aggregates).

The intermolecular forces that hold fibrillizing peptides together in insoluble deposits or plaques are an aspect of "fibrillization" herein as are the intermolecular forces that urge dissolved monomers to aggregate. It will be understood that prevention of fibrillization need not be total to constitute "prevention" as used herein. The extent to which fibrillization has formed insoluble aggregates (or, interchangeably herein, "aggregations") may be evaluated by, for example, measuring in appropriately designed experiments the "thioflavin load" in the brain tissue of experimental animals or the amount of amyloid in the pancreas or other tissues. See Schmidt et al., *Am. J. Pathol.* (1995) 147 pp. 503-515 and Jurgens, C A et al., *Am. J. Pathol.* (2011) 178 pp 2632-2640.

A "subject," used herein interchangeably with the term "patient," can be a human or any other mammal including, without limitation, a primate, rat, mouse, rabbit, pig, cow, sheep, goat, cat or dog. A "subject at risk" or "subject in need thereof", as used herein, is any subject having a condition which, in the judgment of a practitioner of the healing arts, is predictive of the disease. It is not necessary that the subject present any objectively or subjectively recognizable symptom of the disease to be "in need of treatment".

The term "therapy," used interchangeably herein with "treatment," refers to an attempt to prevent or ameliorate an abnormal condition, or the symptoms thereof, in a patient or a subject. It is not intended that "treating" a disease requires curing or eradicating it completely. It is only necessary that the treatment have a therapeutic effect. "Prevention" of a disease or disorder includes the prevention of the recurrence, spread or onset of the disease or disorder. It is not intended that the present invention be limited to complete prevention. For example, delayed onset constitutes prevention herein, as does a reduction in the severity of the disease or disorder. Similarly, the progression of a disease is considered herein to be "reduced" or "inhibited" if, in the judgment of a practitioner of the healing arts, one or more of the characteristic indicia of progression of the disease are reduced or inhibited.

The term "therapeutic effect" refers to the inhibition, activation or replacement of factors causing or contributing to an abnormal, pathological or pathogenic condition, such as an amyloid based disease. A therapeutic effect may or may not relieve all symptoms of the abnormal condition. A prophylactic or preventative effect delays the onset or reduces the severity of one or more of the symptoms or factors causing or contributing to the abnormal condition. In reference to the treatment of abnormal conditions, a "therapeutic effect" can refer, without limitation, to one or more of the following: (a) an increase or decrease in the proliferation, growth, and/or differentiation of cells or the products of cells (such as pancreatic β cells, or the hormones produced in pancreatic β cells) whether those products accumulate within the cells or are released therefrom; (b) enhancing or depressing the function of an affected cell or population of cells e.g., glycemic control, reducing amyloid deposits, which are formed in the islets of Langerhans of diabetic subjects are associated with reduced β-cell mass and are believed to contribute to type 2 diabetes.

An "abnormal condition" as used herein refers to a function in the cells or tissues of an organism that deviates from the normal function in that organism. An abnormal condition, by way of non-limiting examples, includes increased IAPP amyloid deposits in the islets of Langerhans of diabetic subjects, aberrant glycemic control, or dysregulation of hormones produced in pancreatic β cells. Abnormal cell products include metabolic products, hormones and other secreted products, cell signaling agents (whether intracellular or extracellular), elements of intracellular architecture including the cell membrane, "housekeeping" enzymes, and elements of the extracellular matrix. Abnormal cell survival conditions relate to, for example and without limitation, toxic agents of various types, both endogenous and exogenous, can induce cell death.

The abnormal condition, such as an amyloid based disease can be prevented or treated with an identified agent or mutant-hIAPP polypeptide of the present disclosure by contacting such agent or mutant-hIAPP polypeptide to the cells or tissues of the organism either within the organism or outside of the organism. Cells existing outside the organism can be maintained or grown in cell culture dishes, for example. For cells harbored within the organism, many techniques exist in the art to administer substances, including (but not limited to) oral, parenteral, dermal, injection, and aerosol applications. Injections, without limitation, may be made into the bloodstream, into cerebrospinal fluid, epidurally or subdurally, body cavities, and targeted disease sites (e.g., pancreas). For cells outside of the organism, multiple techniques exist in the art to administer the substances, including (but not limited to) cell microinjection techniques, transformation techniques, and carrier techniques.

In a preferred embodiment of the present invention, an abnormal condition is an "amyloid based disease", which as used herein shall mean a pathological condition or disease characterized by the deposition of insoluble ordered protein deposits that are known as amyloid fibrils or amyloid plaques. Amyloid deposition or fibril formation is the pathological marker of many prevalent amyloid based diseases. The process of pancreatic islet amyloid formation and accumulation accelerates the decline of insulin production and secretion in type-2 diabetes, leads to islet cell transplant failure during treatment of type-1 diabetes. In specific embodiments, amyloid based diseases include, but are not limited to, amyloidoses (e.g., any disorder in which amyloid formation causes cell death, organ failure or disease). More particularly, the amyloidoses is diabetes (type-1 or type-2), hyperglycemia, Alzheimer's Disease (AD), Parkinson's Disease (PD), dementia and cerebral amyloid angiopathy (CAA).

The term "therapeutic agent" may be any agent that confers a therapeutic effect on a subject. Non-limiting examples of certain therapeutic agents that can be used in conjunction with the compositions and methods disclosed herein, include insulin or an analog thereof (e.g., Humalog®, Apidra®, NovoLog®, Humulin®, Novolin®, Levemir® or combinations thereof), which may be employed to delivered to a subject at physiological pH.

Compositions

In one aspect of the present disclosure, mutant-hIAPP polypeptides are provided, which are composed of an amino acid sequence that is altered from that of the wild-type hIAPP polypeptide found in rat and humans. Therefore, amino acid residues in the mutant-hIAPP polypeptides of the present disclosure do not correspond to that of endogenous hIAPP proteins, and thus the mutant-hIAPP polypeptides of the present disclosure are not naturally occurring. In certain specific embodiments the mutant-hIAPP polypeptides are soluble at neutral pH. In certain embodiments of the present disclosure novel peptides have been synthesized that are at least 37 amino acids in length and corresponds to at least a portion of the wild-type hIAPP protein as set forth in SEQ ID NO: 1. In other embodiments the mutant-hIAPP polypeptides of the present disclosure contain at least amino acid substitution. In another embodiment the at least one amino acid substitution is at amino acid residue: 18, 20, 24, 25, 26, 28, 29 or any combination thereof. In another embodiment, the mutant-hIAPP polypeptides of the present disclosure contain the following amino acid substitution: H18R, S20R, G24P, A25P, I26P, S28P, S29P or any combination thereof. In certain specific embodiments of the present disclosure the mutant-hIAPP polypeptides include at least the following amino acid substitutions: H18R, G24P, and I26P. In yet another embodiment of the present disclosure the mutant-hIAPP polypeptides include at least the following amino acid substitutions: S20R, G24P, and I26P. In yet another embodiment of the present disclosure, the mutant-hIAPP polypeptides include at least the following amino acid substitutions: H18R, A25P, S28P, S29P. In a specific embodiment the mutant-hIAPP polypeptide includes amino acid substitutions H18R, G24P, and I26P as set forth in SEQ ID NO: 4. In another specific embodiment the mutant-hIAPP polypeptide includes amino acid substitutions S20R, G24P, and I26P as set forth in SEQ ID NO: 5. In yet another specific embodiment of the present disclosure the mutant-hIAPP polypeptide includes amino acid substitutions H18R, A25P, S28P and S29P as set forth in SEQ ID NO: 6. In yet another specific embodiment of the present disclosure the mutant-hIAPP polypeptide includes an amidated c-terminus as set forth in SEQ ID NO: 7, SEQ ID NO: 8, and SEQ ID NO: 9.

In other embodiments, the mutant-hIAPP polypeptides of the present disclosure include a positively charged amino acid substitution at residue 18 and/or 20 (e.g., H18R, S20R) and a single proline residue substitution at a position 24, 25, 26, 28 or 29 (e.g., G24P, A25P, I26P, S28P, S29P). More specifically, the mutant-hIAPP polypeptides of the present disclosure that includes a positively charged amino acid substitution at residue 18 and/or 20 and a single proline residue substitution at a position 24, 25, 26, 28 or 29 have an amino acid sequence of KCNTATCATQRLAN-FLVRSSNNFGAPLSSTNVGSNTY (SEQ ID NO: 10). In yet another non-limiting example a mutant-hIAPP polypeptides of the present disclosure that includes a positively charged amino acid substitution at residue 18 and/or 20 and a single proline residue substitution at a position 24, 25, 26, 28 or 29 has an amidated c-terminus, i.e., KCNTATCATQR-LANFLVRSSNNFGAPLSSTNVGSNTY-NH$_2$ (SEQ ID NO: 11). In certain specific embodiments the mutant-hIAPP polypeptides of the present disclosure include a positively charged amino acid substitution at residue 18 and/or 20 (e.g., H18R, 520R) and a single proline residue substitution at a position 24, 25, 26, 28 or 29 (e.g., G24P, A25P, I26P, S28P, S29P).

The mutant-hIAPP polypeptides of the present disclosure, homologs, and analogs thereof can be synthesized by a number of known techniques. For example, the peptides can be prepared using the solid-phase synthetic technique initially described by Merrifield, in *J. Am. Chem. Soc.* 85, pp. 2149-2154 (1963). Other peptide synthesis techniques can be found in M. Bodanszky, et al., *Peptide Synthesis,* John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Peptides can also be synthesized by solution methods as described in The Proteins, Vol. II. 3d Ed., Neurath, H. et al., Eds., p. 105-237, Academic Press, New York, N.Y. (1976). Appropriate protective groups for use in different peptide syntheses are described in the above-mentioned texts as well as in J. F. W. McOmie, *Protective Groups in Organic Chemistry,* Plenum Press, New York, N.Y. (1973). The polypeptides of the present disclosure can also be prepared by chemical or enzymatic cleavage from larger portions of the amylin protein or from the entire endogenous amylin protein.

Specific examples of conventional techniques include methods such as the Merrifield solid phase technique. In general, the Merrifield solid phase method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine, asparagine, cysteine, glutamine, aspartic acid, glutamic acid, threonine, serine, arginine A preferred method of solid phase synthesis the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The peptide is treated to form the disulfide bond between residues 2 and 7, for example, by incubation in solutions containing dimethyl sulfoxide (DMSO) at room and then purified to yield the final peptide. See, for example, Abedini, A., et al *Anal. Biochem.* (2006) Vol. 351, pp. 181-186.

The mutant-hIAPP peptides of the present disclosure can be recombinantly-produced peptides in accordance with the methods of the present disclosure. Such recombinant DNA techniques known by one of ordinary skill in the art. See, e.g., Current Protocols in Molecular Cloning Ausubel et al., ed. (1995), John Wiley & Sons, New York); Sambrook et al., (1989), Molecular Cloning: A Laboratory Manual, Second Edition, Cold Spring Harbor Laboratory Press, New York; Coligan et al. *Current Protocols in Immunology,* John Wiley & Sons Inc., New York, N.Y. (1994); see, also, Williamson J. A. and Miranker, A. D., Protein Science (2007) Vol. 16, pp. 110-117 (describing the use of an intenin based expression systems that enable the development of amidated c-terminal proteins).

The skilled artisan understands that any of a wide variety of expression systems can be used to provide the recombinant peptides of the present invention. The precise host cell used is not critical to the present methods. The peptides of the present disclosure can be produced in a prokaryotic host (e.g., *E. coli* intenin-based systems), or in a eukaryotic host (e.g., *S. cerevisiae* or mammalian cells, such as COS1, CHO, NIH3T3, and JEG3 cells, or in the cells of an arthropod, for example, *S. frugiperda*). Such cells are available from, for example, the American Type Culture Collection, Manassas, Va. It is appreciated by the skilled artisan that the method of transfection and the choice of expression vehicle will depend on the host system selected. Transformation and transfection methods are described, e.g. in Sambrook et al., (1989); expression vehicles can be chosen from those provided. See, e.g., P. H. Powels et al., Cloning Vectors: A Laboratory Manual. (1985).

For most of the amino acids used to build proteins, more than one coding nucleotide triplet (codon) can code for a particular amino acid residue. This property of the genetic code is known as redundancy. Therefore, a number of different nucleotide sequences can code for a particular peptide corresponding to the mutant-hIAPP polypeptides of the present disclosure. The present disclosure also contemplates a deoxyribonucleic acid (DNA) molecule or segment that defines a gene coding for, i.e., capable of expressing, a subject peptide or a subject chimeric peptide from which a peptide of the present disclosure can be enzymatically or chemically cleaved.

DNA molecules that encode peptides of the present disclosure can be synthesized by chemical techniques, for example, the phosphotriester method of Matteuccie, et al., *J. Am. Chem. Soc.* (1981) Vol. 103, pp. 3185, which is incorporated herein by reference. Using a chemical DNA synthesis technique, desired modifications in the peptide sequence can be made by making substitutions for bases, which code for the native amino acid sequence. Ribonucleic acid equivalents of the above described DNA molecules can also be used.

A nucleic acid molecule comprising a vector capable of replication and expression of a DNA molecule defining coding sequence for a subject polypeptide or subject chimeric polypeptide is also contemplated.

In a preferred embodiment of the present disclosure the mutant-hIAPP polypeptides are synthetic peptides created using Solid-Phase Peptide Synthesis by FMOC Chemistry. For example, a mutant-hIAPP polypeptide is synthesized on a 0.1 mmol scale using a CEM corporation Liberty microwave peptide synthesizer using 9-fluornylmethoxycarbonyl (Fmoc) chemistry. Fmoc protected pseudoproline (oxazolidine) dipeptide derivatives were purchased from Novabiochem. All other reagents were purchased from Advanced Chemtech, PE Biosystems, Sigma, and Fisher Scientific. All solvents used were A.C.S. grade. Use of a 5-(4'-Fmoc-aminomethyl-3',5-dimethoxyphenol) valeric acid (PAL-PEG) resin afforded an amidated C-terminus. Standard Fmoc reaction cycles were used. All amino acids were dissolved in 1-methyl-2-pyrrolidone. Deprotection of Fmoc group was achieved using a mixture of 20% (v/v) piperidine in N,N-dimethylformamide The deprotection was conducted at 40 watts microwave power, with the temperature starting at 30° C. and gradually increasing to 77° C. within the total microwave time of 3 min. Coupling reactions used 0.45 M 2-(1H-benzotriazole-1-yl)-1,1,3,3-tetramethyluronium hexafluorophosphate in N,N-dimethylformamide as the activator and 2 M N,N-Diisopropylethylamine in 1-methyl-2-pyrrolidone as the activator base. The coupling reactions were conducted at 35 watts microwave power, with the temperature starting at 35° C. and gradually increasing to 80° C. within the total microwave time of 5 min. This protocol was used for all residues except Cys, His and Arg. Cys and His were coupled with no microwave power, with the starting temperature of 15° C. and gradually increasing to 48° C. within the total reaction time of 15 min Arg was coupled with no microwave power, with the starting temperature of 15° C. and gradually increasing to 75° C. within the total reaction time of 30 min The first residue attached to the resin, pseudoproline dipeptide derivativesand all β-branched residueswere double coupled. Fmoc-Ala-Thr ($\Psi^{Me,Me}$pro)-OH at position 8-9 , Fmoc-Ser (tBu)-Ser ($\Psi^{Me,Me}$pro) at position 19-20, and Fmoc-Leu-Ser ($\Psi^{Me,Me}$pro)-OH at position 27-28 were utilized when applicable. Peptides were cleaved from the resin using 90% trifluoroacetic acid, 3.33% anisole, 3.33% thioanisole and 3.33% ethanedithiol. The synthesized resin was placed in 6 ml of the cleavage solution and shaken for three hours at room temperature. The reaction mixture was filtered over a 30 ml coarse fitted funnel. The volume of the liquid fraction was reduced by blowing a stream of $N_2$ gas until the sample reached 0.4 ml. The resulting liquid was treated with 30 ml cold diethyl ether to precipitate the crude peptide. The peptide was recovered using a 15 ml fine fitted funnel. The crude peptide was dried overnight by lyophilization. The resulting dry peptide was dissolved in 20% (v/v) acetic acid and then lyophilized before oxidation and purification to improve the solubility of the peptides. The peptides were oxidized in 100% dimethyl sulfoxide at room temperature for 48 to 72 hours with continuous shaking and were then purified via reverse-phase high-performance liquid chromatography (RP-HPLC) using a Vydac C18 preparative column. The Buffers used were 100% (v/v) distilled deionized water with 0.045% HCl as buffer A and 80% (v/v) acetonitrile in distilled deionized water with 0.045% HCl as buffer B. The gradient utilized was 20-60% buffer B in 40 min.

In certain embodiments the Fmoc chemistry includes the incorporation of two or three oxazolidine pseudoproline dipeptide derivatives, with double coupling of alpha-branched residues, pseudoproline dipeptide derivatives, and residues according to the protocol described in Marek, P., et al. *Org. Lett.* (2010) Vol. 12, pp. 4848-4851 and Abedini A., and Raleigh D. *Org. Lett.* (2005) Vol. 7, pp. 693-696 the entire contents of which are incorporated herein by reference.

In another non-limiting embodiment of the present disclosure the mutant-hIAPP can be created using Solid-Phase Peptide Synthesis by T-Boc chemistry. The synthesis of proteins using T-Boc chemistry is well known by those of ordinary skill in the art and certain non-limiting examples of T-Boc Solid-Phase Peptide Synthesis can be found in Schnolzer M., et al., *International Journal of Peptide and Protein Research.* (1992) Vol. 40:3-4, pp. 180-193, the contents of which are incorporated herein by reference.

In certain preferred embodiments the mutant-hIAPP polypeptide compositions of the present disclosure can be isolated and purified from various different sources to a level useful in human therapeutics. In certain embodiments, mutant-hIAPP analogs of the present disclosure can be isolated from the human pancreas in a highly pure state by a combination of: 1) concentration using a centrifuge, 2) gel filtration chromatography, and 3) reverse phase chromatography, specifically HPLC. In, for example, larger scale purification of mutant-hIAPP compositions of the present disclosure, forms of chromatography other than HPLC, such as fast protein liquid chromatography (FPLC) are useful and appropriate. Other forms of chromatography are also useful when isolating and/or purifying mutant-hIAPPs of the present disclosure, such as ion exchange, molecular sieve, or hydrophobic interaction chromatography.

In certain preferred methods, the mutant-hIAPP proteins of the present disclosure are purified to increase solubility, by partially dissolving the crude peptides in 20% acetic acid (v/v), frozen in liquid nitrogen and lyophilized. This procedure can be repeated several times prior to purification. The dry peptides were then redissolved in 35% acetic acid (v/v) and purified via reversed-phase HPLC, using a Vydac C18 preparative column (10 mm×250 mm). A two-buffer system was used, utilizing HCl as the ion pairing agent. Buffer (A) consisted of $H_2O$ and 0.045% HCl (v/v). Buffer (B) consisted of 80% acetonitrile, 20% $H_2O$ and 0.045% HCl (v/v). Purity was checked by HPLC using a Vydac C18 reversed-phase analytical column (4.6 mm×250 mm). Two solvent systems can be used. The first iss the same HCl buffer system used for initial peptide purification. The second buffer system utilized TFA as the ion pairing agent; where buffer (A) consisted of $H_2O$ and 0.1% TFA (v/v) and buffer (B) consisted of 90% acetonitrile, 9.9% $H_2O$ and 0.1% TFA (v/v).

In certain embodiments of the present disclosure, mutant-hIAPPs are oxidized and analyzed by mass spectrometry (e.g., MALDI-TOF) to determine the purity of the mutant-hIAPP polypeptides.

The efficacy of a preparation of the mutant-hIAPP polypeptides of the present disclosure in the treatment of diabetes mellitus is dependent on the ability of the mutant-hIAPP polypeptides to gain access to a subject's circulatory system. Therefore, soluble preparations of mutant-hIAPP polypeptides are required. It has been demonstrated that certain processes can be used to solubilize amylin when present in amyloid masses. See, Cooper, et al., *Proc. Natl. Acad. Sci. USA*, (1987) Vol. 84, pp. 8628-8623. Certain non-limiting examples of solubilizaiton techniques for use in conjunction with the mutant-hIAPP polypeptides of the present disclosure include, dissolution of mutant-hIAPP polypeptides in guanidinium solutions, especially guanidinium hydrochloride, pH 7.5, buffered in 0.2M sodium monohydrogen phosphate/sodium dihydrogen phosphate; the dissolution of mutant-hIAPP polypeptides in trifluoroacetic acid/acetonitrile solutions, especially 1.0% trifluoroacetic acid/67% acetonitrile; the dissolution of mutant-hIAPP polypeptides in formic acid solution, especially 70% formic acid; the use of ultrasound to dissolve mutant-hIAPP polypeptides in a neutral aqueous solution; and lyophilization may render amylin more soluble, perhaps by altering its physical state.

In certain embodiments of the present disclosure, mutant-hIAPP polypeptides may be formulated in aqueous solutions including, but not limited to bacteriostatic water or preservative-free sterile water, preservatives (e.g., metacresol, benzyl alcohol), tonicity modifiers (e.g., D-mannitol), and a pH modifier (e.g., acetic acid and/or sodium acetate). In other embodiments certain inactive ingredients such as, glutamic acid, glycine, polysorbate 20, and sucrose, can be added.

Therapeutic Methods

Deposits of proteinaceous material ("amyloid") accompany a plethora of diseases. So-called amyloid based diseases such as type-1 and type-2 diabetes, hyperglycemia, Alzheimer's disease, bovine spongiform encephalopathy (BSE), Creutzfeldt-Jakob disease (CJD), cerebral amyloid angiopathy ("CAA") and scrapie are all diseases characterized by the presence of amyloid deposits or plaques.

As such, the present disclosure provides methods for the treatment of amyloid based diseases (e.g., diabetes, AD, CAA) by administration of a mutant-hIAPP polypeptide either alone or together with another therapeutic agent described herein (e.g., Humalog®, Apidra®, NovoLog®, Humulin®, Novolin®, Levemir® or combinations thereof).

The instant disclosure provides methods for treating subjects/patients afflicted with an amyloid based disease comprising administering to a subject an effective amount of a mutant-hIAPP polypeptide of the present disclosure. In a preferred aspect, the mutant-hIAPP polypeptide is isolated and substantially purified (e.g., substantially free from substances that limit its effect or produce undesired side-effects).

In certain embodiments, the subject is preferably an animal, including but not limited to animals such as cows, pigs, horses, chickens, cats, dogs, primates, etc., and is preferably a mammal, and most preferably human. In a specific embodiment, a non-human mammal is the subject.

In some embodiments formulations and methods of administration can be employed whereby a mutant-hIAPP polypeptide is provided at a neutral pH in an aqueous solution. In specific embodiments, such mutant-hIAPP polypeptides are formulated at a pH of between 6.8-7.4, 7.0-7.8, 7.0-7.4. In certain preferred embodiments the mutant-hIAPP polypeptides of the present disclosure are formulated at a neutral pH of 7.2-7.4 or 7.4 and provided to a subject in need thereof.

In yet another embodiment, the mutant-hIAPP polypeptide is co-formulated with another therapeutic agent (e.g., Humalog®, Apidra®, NovoLog®, Humulin®, Novolin®, Levemir® or combinations thereof) at a neutral pH as described above; and administered to a subject in need thereof. Additional appropriate formulations and routes of administration are described below.

Various delivery systems are known and can be used to administer the mutant-hIAPP polypeptide of the present disclosure, formulations or co-formulations thereof, e.g., encapsulation in liposomes, microparticles, microcapsules, recombinant cells capable of expressing the compound, receptor-mediated endocytosis (see, e.g., Wu and Wu *J. Biol. Chem.* (1987) Vol. 262, pp. 4429-4432), and construction of a nucleic acid as part of a retroviral or other vector. Methods of introduction can be enteral or parenteral and include but are not limited to intradermal, intramuscular, intraperitoneal, intravenous, subcutaneous, intranasal, epidural, and oral routes. The agents and/or mutant-hIAPP polypeptides of the present disclosure may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the mutant-hIAPP polypeptides of the present disclosure or formulations thereof into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the mutant-hIAPP polypeptides of the instant disclosure, formulations and co-formulations thereof, locally, e.g., by local infusion during surgery, topical application, e.g., by injection, by means of a catheter, or by means of an implant, said implant being of a porous, non-porous, or gelatinous material, including membranes, such as sialastic membranes, or fibers. In one embodiment, administration can be by direct injection into a localized site that is the predominant pathological site of the amyloid based disease, such as, for example, the pancreas.

In another embodiment, the mutant-hIAPP polypeptide of the instant disclosure can be delivered in a vesicle, in particular a liposome (see Langer (1990) *Science* 249:1527-1533; Treat et al., *Liposomes in the Therapy of Infectious Disease and Cancer,* Lopez-Berestein and Fidler (eds.), Liss, New York, pp. 353-365 (1989); Lopez-Berestein, ibid., pp. 317-327; see, generally, ibid.)

In yet another embodiment, the mutant-hIAPP polypeptide of the present disclosure, formulations and co-formulations thereof can be delivered in a controlled release system. In one embodiment, a pump may be used (see Langer, supra; Sefton CRC Crit. Ref. Biomed. Eng. (1987) Vol. 14:201; Buchwald et al. *Surgery* (1980) Vol. 88:507; Saudek et al., *N. Engl. J. Med.* (1989) Vol. 321:574). In another embodiment, polymeric materials can be used (see *Medical Applications of Controlled Release,* Langer and Wise (eds.), CRC Pres., Boca Raton, Fla. (1974); *Controlled Drug Bioavailability, Drug Product Design and Performance,* Smolen and Ball (eds.), Wiley, New York (1984); Ranger and Peppas, J., 1983, *Macromol. Sci. Rev. Macromol. Chem.* Vol. 23:61; see, also, Levy et al. *Science* (1985) 228:190; During et al. *Ann. Neurol.* (1989) 25:351; Howard et al. *J. Neurosurg.* (1989) Vol. 71:105). In yet another embodiment, a controlled release system can be placed in proximity of the therapeutic target area, i.e., a target tissue, thus requiring only a fraction of the systemic dose (see, e.g., Goodson, in Medical Applications of Controlled Release, supra, (1984) Vol. 2, pp. 115-138). Other controlled release systems are discussed in the review by Langer, Science (1990) Vol. 249, pp. 1527-1533).

The mutant-hIAPP polypeptide of the present disclosure, formulations and co-formulations thereof are provided to a subject in a therapeutically effective amount. In preferred embodiments, the mutant-hIAPP polypeptide are delivered by any "pharmaceutically acceptable" means approved by a regulatory agency of the Federal or a state government or listed in the U.S. Pharmacopeia or other generally recognized pharmacopeia for use in animals, and more particularly in humans. In yet another embodiment, the mutant-hIAPP polypeptides of the present disclosure are provided in conjunction with a "carrier", which refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The formulations or co-formulations described herein, if desired, can also contain minor amounts of wetting or emulsifying agents, or pH buffering agents. These formulations can take the form of solutions, suspensions, emulsion, tablets, pills, capsules, powders, sustained-release formulations and the like. The mutant-hIAPP polypeptides can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, the entire contents of which are incorporated by reference herein. Such formulations or co-formulations will contain a therapeutically effective amount of the mutant-hIAPP polypeptides of the present disclosure either alone or in conjunction with other therapeutic agents, preferably in purified form, together with a suitable amount of carrier so as to provide the form for proper administration to the subject. The formulation should suit the mode of administration.

In a preferred embodiment, the mutant-hIAPP polypeptides are formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent (e.g., the mutant-hIAPP polypeptide and insulin). Where the mutant-hIAPP polypeptide is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In another preferred embodiment, the mutant-hIAPP polypeptides of the present disclosure are formulated in a neutral form (e.g., pH 7.0-7.6).

The amount of the mutant-hIAPP polypeptide of the disclosure, which will be effective in the treatment of an amyloid based disease, can be determined by standard clinical techniques based on the present description. In addition, in vitro assays may optionally be employed to help identify optimal dosage ranges. The precise dose to be employed in the formulation or co-formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Certain, non-limiting examples of suitable dosage ranges for injection include, a dose of 0.06 mg/kg/day for an individual having a body weight of 40 kg or less, and such dose may increase or decrease by 0.02 mg/kg to a maximum daily dose of 0.13 mg/kg, a dose of 2.5 mg/day individual having a body weight greater than 40 kg, and such dose may increase or decrease by 1.25 mg to 2.5 mg/day to a maximum dose of 10 mg/day, for females having a body weight greater than 40 kg, a dose of 5 mg/day is appropriate, and such dose may increase or decrease by 1.25 mg to 2.5 mg/day to a maximum dose of 10 mg/day. In yet another example, the mutant-hIAPP polypeptide formulations of the present disclosure can be delivered to a subject in 30 mcg/mL, 60 mcg/mL, 90 mcg/mL or 120 mcg/mL doses.

In yet another embodiment, suitable dosage ranges for intranasal administration are generally about 0.01 pg/kg body weight to 1 mg/kg body weight. Effective doses may be extrapolated from dose-response curves derived from in vitro or animal model test systems.

Protein based drugs are often formulated with "inert" additives such as polymers. Accordingly, therapeutic formulations comprising mutant-hIAPP polypeptide formulations of the present disclosure and at least one pharmaceutically acceptable carrier may further comprise at least one polymer selected from the group consisting of alginates, chitosan, collagen, fibrins, methoxy poly(ethylene glycol), polyanhydrides, poly(caprolactone), poly(ethylene oxide), poly(lactic acid), poly-lactide-co-glycolide (PLGA), poly(ortho esters), polyethylene vinyl-co-acetate (EVAc), polyethylene glycol (PEG), polyester-PEG triblock copolymers, polyphosphazenes, poly[(sebacic-co-(ricinoleic acid)], ricinoleic acid, silicone, and multiple component combinations of the above.

Additionally, mutant-hIAPP polypeptides of the present disclosure may be artificially post-translationally modified with inert, covalently linked polymers such as PEG to slow clearance and increase "bioavailability".

Also encompassed herein are modified forms of the mutant-hIAPP polypeptides of the present disclosure, such as various post-translationally modified forms thereof (e.g., glycosylated forms). Modified variants of the mutant-hIAPP polypeptides of the present disclosure are also envisioned herein. Accordingly, any of the mutant-hIAPP polypeptides disclosed herein can also include a chemical modification selected from the group consisting of amidation, lipidation, glycosylation, pegylation, and combinations thereof. The

EXAMPLES

Example 1

Material and Methods

Peptide Synthesis. All peptides were synthesized on a 0.1 mmol scale using a CEM microwave peptide synthesizer. 9-fluornylmethoxycarbonyl (Fmoc) chemistry was utilized. The 5-(4'-fmoc-aminomethyl-3'5-dimethoxyphenol) valeric acid (PAL-PEG) resin was used to afford an amidated C-terminus. For hIAPP and TM-a and TM-b, Fmoc-protected pseudoproline (oxazolidine) dipeptide derivatives were incorporated to improve the yield as previously described in Abedini, A., and Raleigh, D. P. *Org. Lett.* (2005) Vol. 7, pp. 693-696, the contents of which are incorporated herein by reference. For PM and QM, only Fmoc-Ala-Thr ($\Psi^{Me,Me}$pro)-OH and Fmoc-Leu-Ser ($\Psi^{Me,Me}$pro)-OH were utilized. Standard Fmoc reaction cycles were used as previously described in Marek, P., et al. *Org. Lett.* (2010) Vol. 12, pp. 4848-4851, the contents of which are incorporated herein by reference. The first residue attached to the resin, all β-branched residues, all pseudoproline dipeptide derivatives were double-coupled. The peptides were cleaved from the resin through the use of standard trifluoroacetic acid (TFA) methods.

Oxidation and Purification of Peptides. Crude peptides collected after cleavage were dissolved into 20% (v/v) acetic acid and then lyophilized. This step was repeated several times before oxidation and purification to improve the solubility of the peptides. The peptides were oxidized in 100% dimethyl sulfoxide at room temperature and then were purified via reverse-phase high-performance liquid chromatography (RP-HPLC) using a Vydac C18 preparative column. See, Abedini, A., et al. *Anal. Biochem.* (2006) Vol. 351, pp. 181-186.

The purity of the peptides was checked by analytical HPLC before each experiment. The mass of the pure peptides was confirmed by ionization time-of-flight mass spectrometry. hIAPP, expected 3903.6, observed 3904.6; PM, expected 3949.3, observed 3949.2; H18R-PM, expected 3969.4, observed 3967.1; TM expected 3946.9, observed 3945.7.

Sample Preparation. Each peptide was dissolved into 100% hexafluoroisoproponal (HFIP) to make a 1.6 mM stock solution. Stock solutions were filtered using 0.45 μM Acrodisc syringe filter with a GHP membrane and the required amount of peptide was lyophilized overnight to remove HFIP. Dry peptide was dissolved into the appropriate buffer for the fluorescence assays.

Fluorescence Assays. Thioflavin-T binding assays, conducted without HFIP or stirring at 25° C., were utilized to monitor amyloid formation kinetics. Fluorescence measurements were performed using a Beckman Coulter DTX 880 plate reader with a multimode detector using an excitation wavelength of 430 nm and an emission wavelength of 485 nm. Samples were prepared by dissolving dry peptide into Tris-HCl buffer and thioflavin-T solution immediately before the measurement. The final concentrations were 16 μM hIAPP or 160 μM of each analog and 32 μM thioflavin-T in 20 mM Tris-HCl (pH 7.4).

Solubility Measurements. Dry peptides were dissolved into PBS buffer at pH 7.4 at different initial concentrations, and were incubated for 7 days at 25° C. without stirring. Each sample was then centrifuged using a Beckman Coulter Microfuge 22R Centrifuge at 24° C. for 20 min The relative centrifugal force used was $1.75 \times 10^4$ g. Solubility of each sample was approximated by measuring the absorbance of the corresponding supernatant at 280 nm measured using a Beckman Coulter DU 730 UV/Vis Spectrophotometer. All of the peptides contain a single Tyr, 3 Phe and a disulfide bond, thus their extinction coefficients at 280 nm are very similar.

Transmission Electron Microscopy (TEM). TEM images were collected at the Life Science Microscopy Center at the State University of New York at Stony Brook. 15 μL aliquots of the samples used for fluorescence assays were removed at the end of each kinetic experiment, blotted on a carbon-coated 200-mesh copper grid for 1 min and then negatively stained with saturated uranyl acetate for 1min Circular Dichroism (CD). Far-UV CD experiments were performed on an Applied Photophysics Chirascan CD spectrophotometer at 25° C. Aliquots from the kinetic experiments were removed at the end of each experiment and the spectra were recorded as the average of three repeats over a range of 190-260 nm, at 1 nm intervals. A 0.1 cm quartz cuvette was used and a background spectrum was subtracted from the data.

Cell Culture. Transformed rat insulinoma-1 (INS-1) pancreatic β-cells were grown in RPMI 1640 supplemented with 10% fetal bovine serum (FBS), 11 mM glucose, 10 mM Hepes, 2 mM L-glutamine, 1 mM sodium pyruvate, 50 μM β-mercaptoethanol, 100 U/ml penicillin, and 100 U/ml streptomycin. Cells were maintained at 37° C. under 5% $CO_2$.

AlamarBlue Cell Viability Assays. Cyto-toxicity was measured by AlamarBlue reduction assays. INS-1 β-cells were seeded at a density of 30,000 cells per well in 96-well plates and cultured for 24 hours prior to stimulation with wild type human LAPP, rat LAPP and soluble LAPP analogs. Peptides were dissolved directly in complete RPMI and added to cells. Peptide solutions were incubated on cells for 24 to 48 hours. AlamarBlue was diluted ten-fold in culture media and incubated on cells for 5 hours at 37° C. Fluorescence (excitation 530; emission 590 nm) was measured on a Beckman Coulter DTX880 fluorescent plate reader. Values were calculated relative to those of control cells treated without peptide. All values represent means±SEM (n=4).

Light microcopy. Changes in cell morphology were examined by light microscopy to evaluate cell viability. Transformed rat INS-1 β-cells were photographed after 5 hours of incubation at experimental conditions, prior to assessment of toxicity by AlamarBlue cell viability assays. Images were captured using the Nikon Eclipse TiE/B automated fluorescent microscope with Photometrics HQ Monochrome digital camera.

Example 2

Mutant hIAPP Polypeptides do not form Amyloid

After creating mutant hIAPP polypeptides of the present disclosure, applicants tested the propensity of the different analogs to form amyloid at pH 7.4 using thioflavin-T fluorescence assays. Thioflavin-T is a small dye that experiences an increase in quantum yield upon binding to amyloid fibrils, and has been shown to not perturb the kinetics of hIAPP formation. Amyloid formation follows a sigmoidal time course consisting of a lag phase in which few, if any, fibrils are formed, followed by a growth phase and a saturation phase in which amyloid fibrils are in equilibrium with soluble peptide. Amyloid formation by hIAPP reaches the saturation phase within 40 hours, while none of the analogs tested (PM, TM-a,b, DM and QM) formed any amyloid during the time course of the experiments (about 140 hrs) as indicated by flat fluorescence curves, even though they were at a 10-fold higher concentration than hIAPP (FIG. 2A-C).

Samples were further analyzed using TEM and CD. The TEM image of hIAPP showed typical amyloid fibril morphology, while no fibrils were found in the TEM images of the hIAPP analogs (PM, TM-a, b, DM and QM) (FIG. 3B-F). The CD results are consistent with the fluorescence experiments and the TEM studies; the spectrum of hIAPP showed β-sheet structure, while the spectra of the three analogs all indicated random structures (FIG. 2D-G).

Example 3

The Analogs are Significantly more Soluble than PM at Neutral pH

The solubility of PM and the mutant hIAPP polypeptides of the present disclosure was analyzed and compared at pH 7.4. Each peptide was incubated in buffer for 7 days at three different concentrations (100 μM, 500 μM and 1 mM) and the solution was then centrifuged. The apparent solubility was represented by the absorbance of the supernatant of each sample measured at 280 nm. The extinction coefficients of all polypeptides are very similar at 280 nm since they all contain the same aromatic residues and each contains a disulfide bond. A sample of hIAPP at 1 mM was used as a control. At 100 μM, TM-b exhibited an increase in solubility over that of PM as shown by the absorbance of the soluble fraction of TM-b, TM-a and PM sample is 0.155, 0.103 and 0.112, respectively. Additionally, the supernatant of QM sample has a higher absorbance, 0.162, than that of TM-a and PM, 0.103 and 0.112 respectively (FIG. 4A). However, at higher concentrations (500 μM and 1 mM), the amount of peptide remaining in solution was significantly higher for both analogs compared to PM. At 1 mM, the absorbance of the soluble fraction of TM-a, TM-b and QM were 1.23, 1.49, and 1.33 respectively, while that value of PM was only 0.354. In comparison, the absorbance of the supernatant of the 1 mM hIAPP was 0.109 (FIG. 4). At 500 μM, the absorbance of the supernatant of TM-a, TM-b, and QM were 0.609, 0.785 and 0.716 respectively, and both were still significantly higher than that of PM, 0.330 (FIG. 4). Taken together, these results clearly show that the mutant hIAPP polpeptides of the present disclosure are significantly more soluble than wild-type hIAPP and existing hIAPP analogs (i.e., pramlintide) at neutral pH.

Example 4

Neither TM-a nor QM hIAPP Mutant Polypeptides Exhibit Toxicity in β-Cells

The effects of the mutant hIAPP polypeptides on cell viability using rat INS-1 β-cells, a pancreatic cell line that is commonly employed in studies of hIAPP toxicity. Cell viability was monitored by AlamarBlue assays conducted at both 30 μM and 60 μM. hIAPP was used as a positive control. Incubating INS-1 β-cells with 30 μM wild-type hIAPP lead to clearly distinguishable toxicity; cell viability was reduced to 62±4% relative to the media control after 24 hour incubation and 54±5% after 48 hour incubation. In contrast, incubation of cells with either TM-a or QM polypeptides at 30 μM revealed no significant decrease in cell viability (FIG. 5). Moreover, increasing the wild-type hIAPP concentration to 60 μM resulted in even more significant cell toxicity; cell viability was reduced to only 14±9% after 24 hour incubation and 9±9% after 48 hour incubation. Unexpected and surprising results show no cytotoxicity for cells treated with TM-a or QM at 60 μM (FIG. 6), demonstrating that, unlike wild-type hIAPP, mutant hIAPP polypeptides, TM and QM are not toxic to cells at varying concentrations.

Example 5

DM Mutant-hIAPP Polypeptides do not Form Amyloid and Show Improved Solubility at Physiological pH over PM The instant disclosure shows that multiple proline substitutions are not required to accompany the charged mutations in order to improve the solubility at neutral pH. For example, the H18R, I26P double mutant of hIAPP (DM) as set forth in SEQ ID NO: 10 and 11 did not form amyloid, as demonstrated by a flat thioflavin-T fluorescence curve (FIG. 2C) and by TEM images (FIG. 3F). Additionally, DM showed a much better solubility at neutral pH than PM, similar to the behavior of TM-a and TM-b, each of which has one more Pro substitution in the sequence (FIG. 4C). The absorbance of the soluble fraction of 1 mM, 500 μM, and 100 μM samples of DM measured after one week incubation is 1.18 for the 1 mM sample, 0.673 for the 500 μM sample, and 0.104 for the 100 μM sample.

What is claimed is:

1. An isolated mutant-human islet amyloid polypeptide (hIAPP) selected from the group consisting of SEQ ID NO: 4, SEQ ID NO: 6, SEQ ID NO: 7, SEQ ID NO: 9, SEQ ID NO: 10 and SEQ ID NO: 11.

2. The isolated mutant-hIAPP polypeptide of claim 1, wherein said polypeptide is formulated at neutral pH.

3. The isolated mutant-hIAPP polypeptide of claim 2, wherein said neutral pH is between 7.0 and 7.8.

4. The isolated mutant hIAPP polypeptide of claim 3, wherein said neutral pH is between 7.2 and 7.4.

5. The isolated mutant hIAPP polypeptide of claim 4, wherein said neutral pH is 7.4.

6. The isolated mutant-hIAPP polypeptide of claim 1, wherein said polypeptide is a synthetic peptide.

\* \* \* \* \*